(12) United States Patent
Eriksson et al.

(10) Patent No.: US 7,517,897 B2
(45) Date of Patent: Apr. 14, 2009

(54) DERIVATIVES OF 6,7-DIHYDRO-5H-IMIDAZO[1,2-A] IMIDAZOLE-3-SULFONIC ACID

(75) Inventors: Magnus Carl Arne Eriksson, Brookfield, CT (US); Rene Marc Lemieux, Plantsville, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 34 days.

(21) Appl. No.: 11/382,940

(22) Filed: May 12, 2006

(65) Prior Publication Data

US 2006/0264472 A1    Nov. 23, 2006

Related U.S. Application Data

(60) Provisional application No. 60/682,462, filed on May 19, 2005.

(51) Int. Cl.
*A01N 43/52* (2006.01)
(52) U.S. Cl. .................... 514/393; 514/338; 546/273.1; 548/303.1
(58) Field of Classification Search .................... None
See application file for complete search history.

(56) References Cited

U.S. PATENT DOCUMENTS 6,355,664 B1    3/2002    Kelly et al.
6,492,408 B1 *  12/2002   Wu et al. .................... 514/387
6,844,360 B2    1/2005    Kelly et al.
6,852,748 B1    2/2005    Kelly et al.
2006/0025447 A1  2/2006   Wang et al.
2006/0229287 A1  10/2006  Brunette

FOREIGN PATENT DOCUMENTS

| WO | 9839303 | | 9/1998 |
| WO | 0107440 | A1 | 2/2001 |
| WO | 2004041273 | A1 | 5/2004 |
| WO | 2004041827 | A2 | 5/2004 |

OTHER PUBLICATIONS

Wu, et al; Second-Generation Lymphocyte Function-Associated Antigen-1 Inhibitors: 1H-Imidazo[1,2-a] imidazol-2-one Derivatives; Journal of Medicinal Chemistry, American Chemical Society, Washington, US: vol. 47: Sep. 29, 2004; pp. 5356-5366.
International Search Report for PCT/US2006/016903.

* cited by examiner

*Primary Examiner*—Deborah D Carr
(74) *Attorney, Agent, or Firm*—Michael P. Morris; Mary-Ellen M. Devlin; Philip I. Datlow

(57) ABSTRACT

Derivatives of 6,7-dihydro-5H-imidazo[1,2-a]imidazole-3-sulfonic acid which exhibit good inhibitory effect upon the interaction of CAMs and Leukointegrins and are thus useful in the treatment of inflammatory disease.

19 Claims, No Drawings

DERIVATIVES OF 6,7-DIHYDRO-5H-IMIDAZO[1,2-A] IMIDAZOLE-3-SULFONIC ACID

This application claims the benefit of U.S. Provisional Application No. 60/682,462, filed on May 19, 2005.

BACKGROUND OF THE INVENTION

1. Technical Field

The present invention relates generally to a class of derivatives of 6,7-dihydro-5H-imidazo[1,2-a]imidazole-3-sulfonic acid, the synthesis of these compounds, their use in the treatment of inflammatory disease, and pharmaceutical compositions comprising these compounds.

2. Background Information

Research spanning the last decade has helped to elucidate the molecular events attending cell-cell interactions in the body, especially those events involved in the movement and activation of cells in the immune system. See generally, Springer, T. *Nature,* 1990, 346, 425-434. Cell surface proteins, and especially the Cellular Adhesion Molecules ("CAMs") and "Leukointegrins", including LFA-1, MAC-1 and p150,95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently believed that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2, ICAM-3 or ICAM-4 which are expressed on blood vessel endothelial cell surfaces and on other leukocytes. The interaction of the CAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally Kishimoto, T. K.; Rothlein; R. R. *Adv. Pharmacol.* 1994, 25, 117-138 and Diamond, M.; Springer, T. *Current Biology,* 1994, 4, 506-517.

A group of individuals has been identified which lack the appropriate expression of Leukointegrins, a condition termed "Leukocyte Adhesion Deficiency" (Anderson, D. C.; et al., *Fed. Proc.* 1985, 44, 2671-2677 and Anderson, D. C.; et al., *J. Infect. Dis.* 1985, 152, 668-689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD18 family. By virtue of the fact that LAD patients who lack CD18 cannot mount an inflammatory response, it is believed that antagonism of CD18, CD11/ICAM interactions will also inhibit an inflammatory response.

It has been demonstrated that the antagonism of the interaction between the CAMs and the Leukointegrins can be realized by agents directed against either component. Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to CAMs or Leukointegrins include antigen or mitogen-induced lymphocyte proliferation, homotypic aggregation of lymphocytes, T-cell mediated cytolysis and antigen-specific induced tolerance. The relevance of the in vitro studies are supported by in vivo studies with antibodies directed against ICAM-1 or LFA-1. For example, antibodies directed against LFA-1 can prevent thyroid graft rejection and prolong heart allograft survival in mice (Gorski, A.; *Immunology Today,* 1994, 15, 251-255). Of greater significance, antibodies directed against ICAM-1 have shown efficacy in vivo as anti-inflammatory agents in human diseases such as renal allograft rejection and rheumatoid arthritis (Rothlein, R. R.; Scharschmidt, L., in: *Adhesion Molecules,* Wegner, C. D., Ed., 1994, 1-8; Cosimi, C. B., et al., *J. Immunol.* 1990, 144, 4604-4612 and Kavanaugh, A. et al., *Arthritis Rheum.* 1994, 37, 992-1004) and antibodies directed against LFA-1 have demonstrated immunosuppressive effects in bone marrow transplantation and in the prevention of early rejection of renal allografts (Fischer, A.; et al., *Lancet,* 1989, 2, 1058-1060 and Le Mauff, B.; et al., *Transplantation,* 1991, 52, 291-295).

It has also been demonstrated that a recombinant soluble form of ICAM-1 can act as an inhibitor of the ICAM-1 interaction with LFA-1. Soluble ICAM-1 acts as a direct antagonist of CD18,CD11/ICAM-1 interactions on cells and shows inhibitory activity in in vitro models of immune response such as the human mixed lymphocyte response, cytotoxic T cell responses and T cell proliferation from diabetic patients in response to islet cells (Becker, J. C.; et al., *J. Immunol.* 1993, 151, 7224 and Roep, B. O.; et al., *Lancet,* 1994, 343, 1590).

Thus, the prior art has demonstrated that large protein molecules which antagonize the binding of the CAMs to the Leukointegrins have therapeutic potential in mitigating inflammatory and immunological responses often associated with the pathogenesis of many autoimmune or inflammatory diseases. However proteins have significant deficiencies as therapeutic agents, including the inability to be delivered orally and potential immunoreactivity which limits the utility of theses molecules for chronic administration. Furthermore, protein-based therapeutics are generally expensive to produce.

It follows that small molecules having the similar ability as large protein molecules to directly and selectively antagonize the binding of the CAMs to the Leukointegrins would make preferable therapeutic agents.

Several small molecules have been described in the literature that affect the interaction of CAMs and Leukointegrins. For example, U.S. Pat. No. 6,355,664 and the corresponding WO 98/39303 disclose a class of small molecule, having a hydantoin core, that are inhibitors of the interaction of LFA-1 and ICAM-1. Of greater relevance to the present invention is U.S. Pat. No. 6,492,408, which discloses compounds that instead have an 6,7-dihydro-5H-imidazo[1,2-a]imidazole core. While the compounds that are specifically described by U.S. Pat. No. 6,492,408 have a more potent inhibitory affect upon the interaction of CAMs and Leukointegrins than do the hydantoins of U.S. Pat. No. 6,355,664 and the corresponding WO9839303, they nevertheless are not ideal therapeutic agents because the rate at which they are metabolized is undesirably high. Additional inhibitors of the interaction of LFA-1 and ICAM-1 having the 6,7-dihydro-5H-imidazo[1,2-a]imidazole core structure are described in U.S. Pat. Nos. 6,844,360 and 6,852,748.

The problem to be solved by the present invention is to find additional small molecules that have good inhibitory effect upon the interaction of CAMs and Leukointegrins, while also having an acceptable metabolic profile.

BRIEF SUMMARY OF THE INVENTION

The compounds of the present invention are a subset or selection of the 6,7-dihydro-5H-imidazo[1,2-a]imidazoles that are generically but not specifically described by U.S. Pat. No. 6,492,408. The compounds of the present invention are potent inhibitors of the interaction of LFA-1 and ICAM-1, and are therefore useful in the treatment of inflammatory diseases. In addition, representative compounds of the present invention have either been shown to have, or are expected to have, an improved metabolic profile, e.g., an improved metabolic stability. Particular embodiments of the invention include: the compounds of formula (I) and the pharmaceutically acceptable salts thereof, pharmaceutical compositions comprising a compound of the formula (I), or a pharmaceutically acceptable salt thereof, and one or more pharmaceutically acceptable carriers or advjuvants; and methods for the treatment of an inflammatory condition as described herein comprising administering to a patient in need thereof a therapeutically effective amount of a compound of the formula (I), or a pharmaceutically acceptable salt thereof.

DETAILED DESCRIPTION OF THE INVENTION

The invention comprises compounds of the formula I

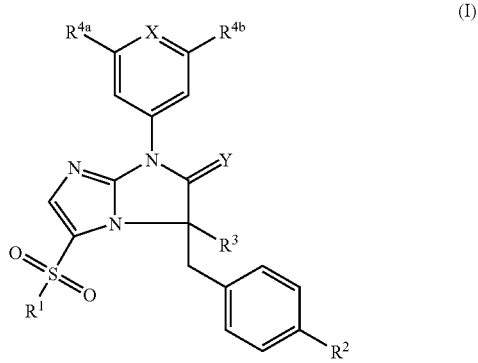

(I)

wherein:
$R^1$ is: OH or $NH_2$;
$R^2$ is:
  (A) aryl selected from the group consisting of pyridyl and pyrimidyl, wherein one or more hydrogen atoms of said aryl group are independently substituted with moieties selected from the group consisting of:
    (i) cyano,
    (ii) halogen and
    (iii) groups of the formula —$NR^{13}R^{14}$, wherein $R^{13}$ and $R^{14}$ are each, independently, hydrogen or straight or branched alkyl of 1 to 3 carbon atoms;
  (B) trifluoromethoxy or,
  (C) cyano;
$R^3$ is straight or branched alkyl of 1 to 3 carbon atoms;
$R^{4a}$ is halogen or alkyl of 1 to 2 carbon atoms substituted by one or more halogen atoms;
$R^{4b}$ is halogen or alkyl of 1 to 2 carbon atoms substituted by one or more halogen atoms;
X is —CH= or —N=; and
Y is an oxygen or sulfur atom;
  or a pharmaceutically acceptable salt thereof.

Below are some preferred embodiments of the various variable groups in the Compound of Formula (I):
(A) Definitions of $R^1$:
(Ai) $R^1$ is OH
(Aii) $R^1$ is $NH_2$
(B) Definitions of $R^2$:
(Bi) $R^2$ is:
  (A) aryl selected from the group consisting of 3-pyridyl and 5-pyrimidyl, wherein said aryl group is mono-, di- or tri-substituted with:
    (i) cyano;
    (ii) halogen; or
    (iii) $NH_2$;
  (B) trifluoromethoxy; or
  (C) cyano;
(Bii) $R^2$ is:
  (A) aryl selected from the group consisting of 3-pyridyl and 5-pyrimidyl wherein said aryl group is monosubstituted with:
    (i) cyano or
    (ii) $NH_2$,
  (B) trifluoromethoxy; or
  (C) cyano;
(Biii) $R^2$ is: (A) 5-pyrimidyl monosubstituted with $NH_2$:
  (B) trifluoromethoxy or
  (C) cyano;
(C) Definitions of $R^3$:
(Ci) $R^3$ is methyl or ethyl;
(Cii) $R^3$ is methyl.
(D) Definitions of $R^{4a}$:
(Di) $R^{4a}$ is Cl or $CF_3$;
(Dii) $R^{4a}$ is Cl;
(Diii) $R^{4a}$ is $CF_3$
(E) Definitions of $R^{4b}$:
(Ei) $R^{4b}$ is Cl or $CF_3$;
(Eii) $R^{4b}$ is Cl;
(Eiii) $R^{4b}$ is $CF_3$
(F) Definitions of X:
(Fi) X is —CH—;
(Fii) X is —N=.
(G) Definitions of Y:
(Gi) Y is oxygen;
(Gii) Y is sulfur Any and each of the above definitions (Ai) to (Gii) may be combined with each other in any combination to obtain particular subgeneric definitions for the compounds of Formula (I).

The following table represents further subgeneric embodiments I-1 to I-45 of the compounds of Formula (I) wherein the variable groups in the table are defined according to the definitions (Ai) to (Gii) set forth above:

| Embodiment | $R^1$ | $R^2$ | $R^3$ | $R^{4a}$ | $R^{4b}$ | X | Y |
|---|---|---|---|---|---|---|---|
| I-1 | Ai or Aii | Bi | Ci | Di | Ei | Fi | Gi |
| I-2 | Ai or Aii | Bii | Ci | Di | Ei | Fi | Gi |
| I-3 | Ai or Aii | Bii | Cii | Di | Ei | Fi | Gi |
| I-4 | Ai or Aii | Bii | Cii | Dii | Eii | Fi | Gi |
| I-5 | Ai or Aii | Bii | Cii | Dii | Eii | Fi | Gii |
| I-6 | Ai or Aii | Bii | Cii | Dii | Eii | Fii | Gi |
| I-7 | Ai or Aii | Bii | Cii | Dii | Eii | Fii | Gii |
| I-8 | Ai or Aii | Bii | Cii | Dii | Eiii | Fi | Gi |
| I-9 | Ai or Aii | Bii | Cii | Dii | Eiii | Fi | Gii |
| I-10 | Ai or Aii | Bii | Cii | Dii | Eiii | Fii | Gi |
| I-11 | Ai or Aii | Bii | Cii | Dii | Eiii | Fii | Gii |
| I-12 | Ai or Aii | Biii | Ci | Di | Ei | Fi | Gi |
| I-13 | Ai or Aii | Biii | Cii | Di | Ei | Fi | Gi |
| I-14 | Ai or Aii | Biii | Cii | Dii | Eii | Fi | Gi |
| I-15 | Ai or Aii | Biii | Cii | Dii | Eii | Fi | Gii |
| I-16 | Ai or Aii | Biii | Cii | Dii | Eii | Fii | Gi |
| I-17 | Ai or Aii | Biii | Cii | Dii | Eii | Fii | Gii |
| I-18 | Ai or Aii | Biii | Cii | Dii | Eiii | Fi | Gi |

-continued

| Embodiment | R$^1$ | R$^2$ | R$^3$ | R$^{4a}$ | R$^{4b}$ | X | Y |
|---|---|---|---|---|---|---|---|
| I-19 | Ai or Aii | Biii | Cii | Dii | Eiii | Fi | Gii |
| I-20 | Ai or Aii | Biii | Cii | Dii | Eiii | Fii | Gi |
| I-21 | Ai or Aii | Biii | Cii | Dii | Eiii | Fii | Gii |
| I-22 | Ai | Bi | Ci | Di | Ei | Fi | Gi |
| I-23 | Ai | Bii | Ci | Di | Ei | Fi | Gi |
| I-24 | Ai | Biii | Ci | Di | Ei | Fi | Gi |
| I-25 | Ai | Biii | Cii | Di | Ei | Fi | Gi |
| I-26 | Ai | Biii | Cii | Dii | Eii | Fi | Gi |
| I-27 | Ai | Biii | Cii | Dii | Eii | Fi | Gii |
| I-28 | Ai | Biii | Cii | Dii | Eii | Fii | Gi |
| I-29 | Ai | Biii | Cii | Dii | Eii | Fii | Gii |
| I-30 | Ai | Biii | Cii | Dii | Eiii | Fi | Gi |
| I-31 | Ai | Biii | Cii | Dii | Eiii | Fi | Gii |
| I-32 | Ai | Biii | Cii | Dii | Eiii | Fii | Gi |
| I-33 | Ai | Biii | Cii | Dii | Eiii | Fii | Gii |
| I-34 | Aii | Bi | Ci | Di | Ei | Fi | Gi |
| I-35 | Aii | Bii | Ci | Di | Ei | Fi | Gi |
| I-36 | Aii | Biii | Ci | Di | Ei | Fi | Gi |
| I-37 | Aii | Biii | Cii | Di | Ei | Fi | Gi |
| I-38 | Aii | Biii | Cii | Dii | Eii | Fi | Gi |
| I-39 | Aii | Biii | Cii | Dii | Eii | Fi | Gii |
| I-40 | Aii | Biii | Cii | Dii | Eii | Fii | Gi |
| I-41 | Aii | Biii | Cii | Dii | Eii | Fii | Gii |
| I-42 | Aii | Biii | Cii | Dii | Eiii | Fi | Gi |
| I-43 | Aii | Biii | Cii | Dii | Eiii | Fi | Gii |
| I-44 | Aii | Biii | Cii | Dii | Eiii | Fii | Gi |
| I-45 | Aii | Biii | Cii | Dii | Eiii | Fii | Gii |

It will be appreciated that the compounds of the formula I have one chiral center.

In an ultimately preferred generic aspect, the invention includes compounds of formula I with the absolute stereochemistry depicted below in formula I*.

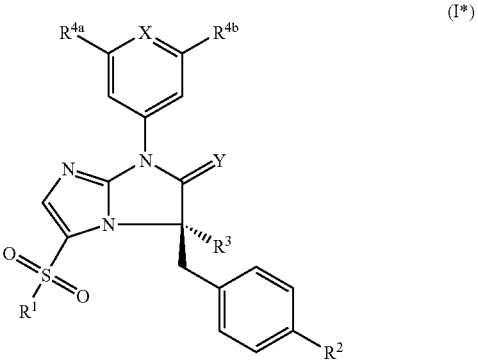

(I*)

Specifically preferred are compounds of the formula I selected from the compounds in the following Table I:

TABLE I

| Compound Number | STRUCTURE | NAME |
|---|---|---|
| 1 | 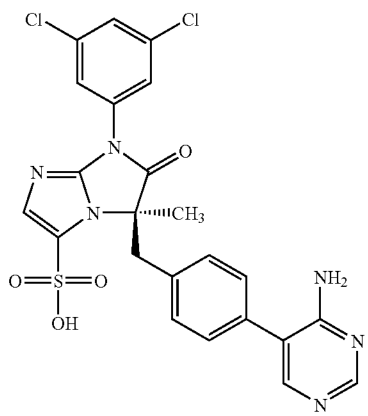 | (R)-5-[4-(4-Amino-pyrimidin-5-yl)-benzyl]-7-(3,5-dichloro-phenyl)-5-methyl-6-oxo-6,7-dihydro-5H-imidazo[1,2-a]imidazole-3-sulfonic acid |
| 2 | 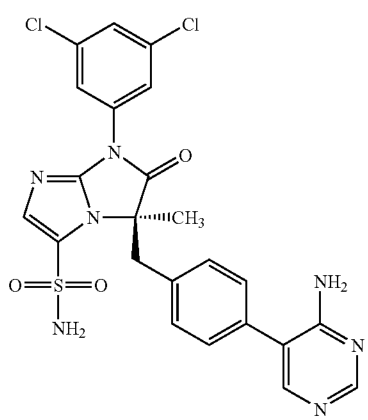 | (R)-5-[4-(4-Amino-pyrimidin-5-yl)-benzyl]-7-(3,5-dichloro-phenyl)-5-methyl-6-oxo-6,7-dihydro-5H-imidazo[1,2-a]imidazole-3-sulfonic acid amide |

TABLE I-continued

| Compound Number | STRUCTURE | NAME |
|---|---|---|
| 3 | 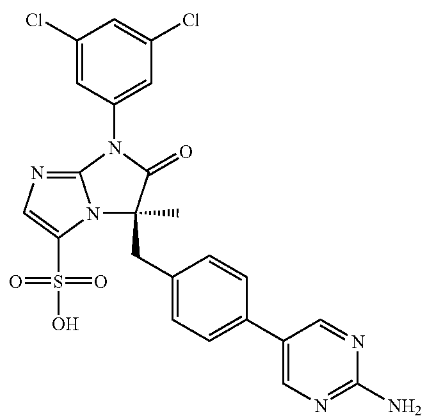 | (R)-5-[4-(2-Amino-pyrimidin-5-yl)-benzyl]-7-(3,5-dichloro-phenyl)-5-methyl-6-oxo-6,7-dihydro-5H-imidazo[1,2-a]imidazole-3-sulfonic acid |
| 4 | 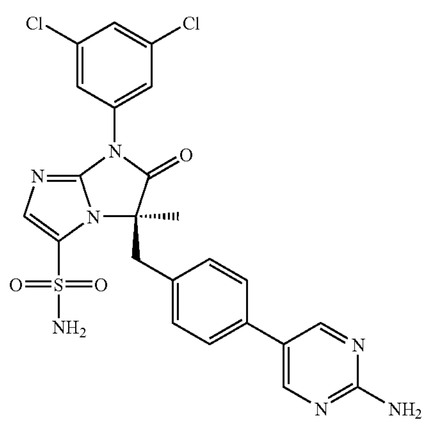 | (R)-5-[4-(2-Amino-pyrimidin-5-yl)-benzyl]-7-(3,5-dichloro-phenyl)-5-methyl-6-oxo-6,7-dihydro-5H-imidazo[1,2-a]imidazole-3-sulfonic acid amide |
| 5 | 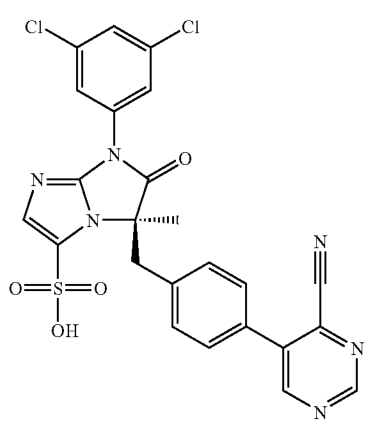 | (R)-5-[4-(4-Cyano-pyrimidin-5-yl)-benzyl]-7-(3,5-dichloro-phenyl)-5-methyl-6-oxo-6,7-dihydro-5H-imidazo[1,2-a]imidazole-3-sulfonic acid |

TABLE I-continued

| Compound Number | STRUCTURE | NAME |
|---|---|---|
| 6 | 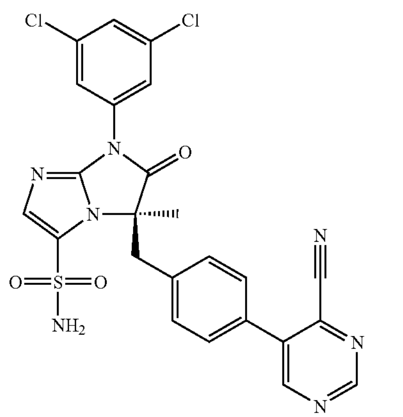 | (R)-5-[4-(4-Cyano-pyrimidin-5-yl)-benzyl]-7-(3,5-dichloro-phenyl)-5-methyl-6-oxo-6,7-dihydro-5H-imidazo[1,2-a]imidazole-3-sulfonic acid amide |
| 7 | 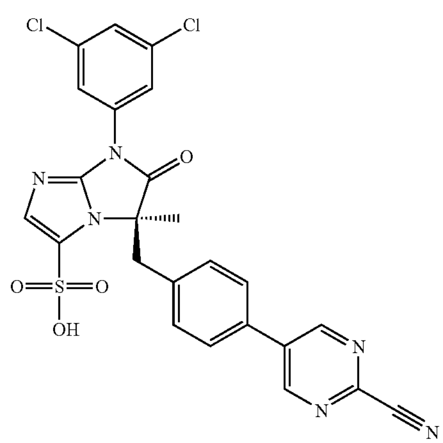 | (R)-5-[4-(2-Cyano-pyrimidin-5-yl)-benzyl]-7-(3,5-dichloro-phenyl)-5-methyl-6-oxo-6,7-dihydro-5H-imidazo[1,2-a]imidazole-3-sulfonic acid |
| 8 | 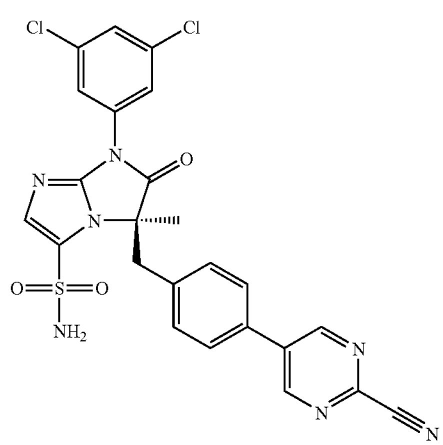 | (R)-5-[4-(2-Cyano-pyrimidin-5-yl)-benzyl]-7-(3,5-dichloro-phenyl)-5-methyl-6-oxo-6,7-dihydro-5H-imidazo[1,2-a]imidazole-3-sulfonic acid amide |

TABLE I-continued

| Compound Number | STRUCTURE | NAME |
|---|---|---|
| 9 | 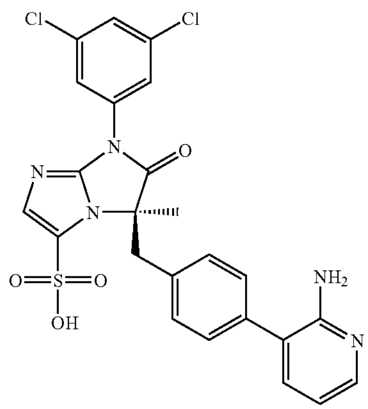 | (R)-5-[4-(2-Amino-pyridin-3-yl)-benzyl]-7-(3,5-dichloro-phenyl)-5-methyl-6-oxo-6,7-dihydro-5H-imidazo[1,2-a]imidazole-3-sulfonic acid |
| 10 | 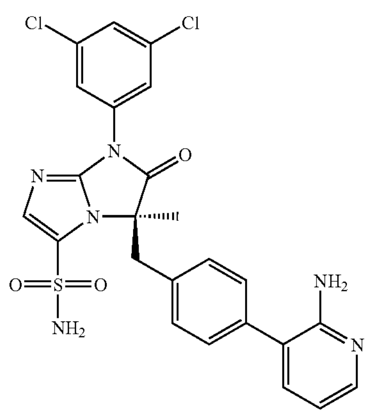 | (R)-5-[4-(2-Amino-pyridin-3-yl)-benzyl]-7-(3,5-dichloro-phenyl)-5-methyl-6-oxo-6,7-dihydro-5H-imidazo[1,2-a]imidazole-3-sulfonic acid amide |
| 11 | 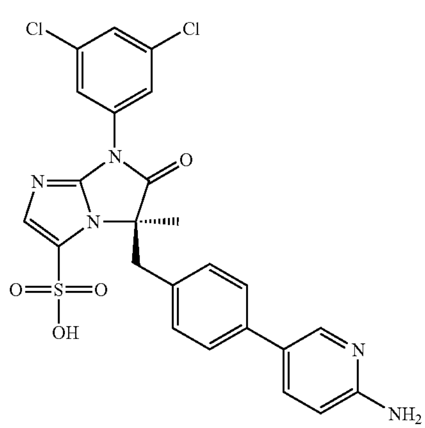 | (R)-5-[4-(6-Amino-pyridin-3-yl)-benzyl]-7-(3,5-dichloro-phenyl)-5-methyl-6-oxo-6,7-dihydro-5H-imidazo[1,2-a]imidazole-3-sulfonic acid |

TABLE I-continued
| Compound Number | STRUCTURE | NAME |
|---|---|---|
| 12 | 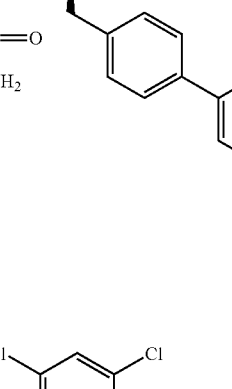 | (R)-5-[4-(6-Amino-pyridin-3-yl)-benzyl]-7-(3,5-dichloro-phenyl)-5-methyl-6-oxo-6,7-dihydro-5H-imidazo[1,2-a]imidazole-3-sulfonic acid amide |
| 13 | 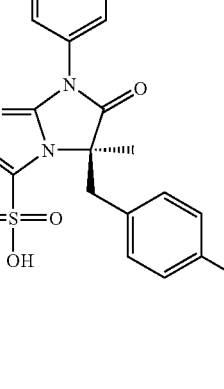 | (R)-5-[4-(2-Cyano-pyridin-3-yl)-benzyl]-7-(3,5-dichloro-phenyl)-5-methyl-6-oxo-6,7-dihydro-5H-imidazo[1,2-a]imidazole-3-sulfonic acid |
| 14 | 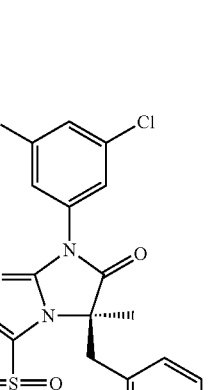 | (R)-5-[4-(2-Cyano-pyridin-3-yl)-benzyl]-7-(3,5-dichloro-phenyl)-5-methyl-6-oxo-6,7-dihydro-5H-imidazo[1,2-a]imidazole-3-sulfonic acid amide |

TABLE I-continued

| Compound Number | STRUCTURE | NAME |
|---|---|---|
| 15 | 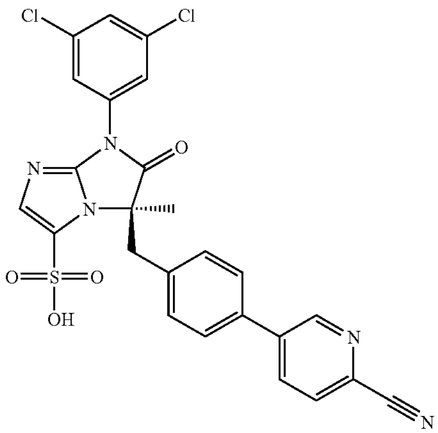 | (R)-5-[4-(6-Cyano-pyridin-3-yl)-benzyl]-7-(3,5-dichloro-phenyl)-5-methyl-6-oxo-6,7-dihydro-5H-imidazo[1,2-a]imidazole-3-sulfonic acid |
| 16 | 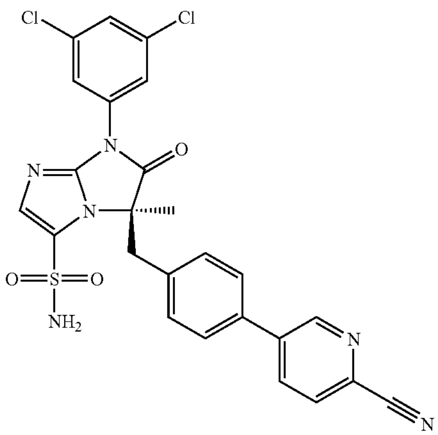 | (R)-5-[4-(6-Cyano-pyridin-3-yl)-benzyl]-7-(3,5-dichloro-phenyl)-5-methyl-6-oxo-6,7-dihydro-5H-imidazo[1,2-a]imidazole-3-sulfonic acid amide |
| 17 | 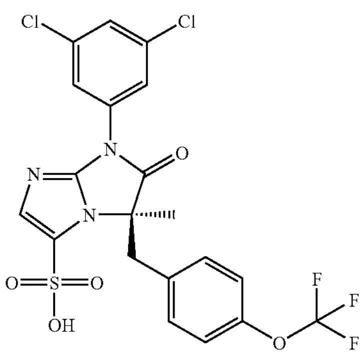 | (R)-7-(3,5-Dichloro-phenyl)-5-methyl-6-oxo-5-(4-trifluoromethoxy-benzyl)-6,7-dihydro-5H-imidazo[1,2-a]imidazole-3-sulfonic acid |
| 18 | 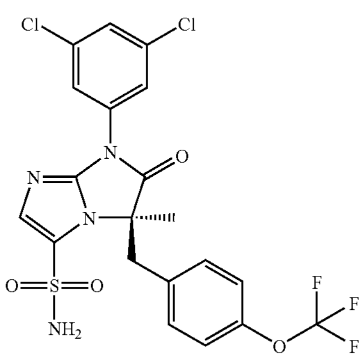 | (R)-7-(3,5-Dichloro-phenyl)-5-methyl-6-oxo-5-(4-trifluoromethoxy-benzyl)-6,7-dihydro-5H-imidazo[1,2-a]imidazole-3-sulfonic acid amide |

TABLE I-continued

| Compound Number | STRUCTURE | NAME |
|---|---|---|
| 19 | 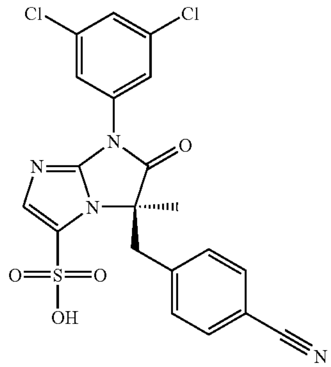 | (R)-5-(4-Cyano-benzyl)-7-(3,5-dichloro-phenyl)-5-methyl-6-oxo-6,7-dihydro-5H-imidazo[1,2-a]imidazole-3-sulfonic acid |
| 20 | 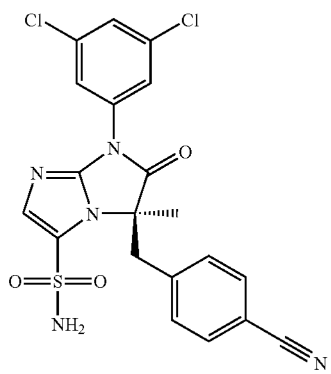 | (R)-5-(4-Cyano-benzyl)-7-(3,5-dichloro-phenyl)-5-methyl-6-oxo-6,7-dihydro-5H-imidazo[1,2-a]imidazole-3-sulfonic acid amide |
| 21 | 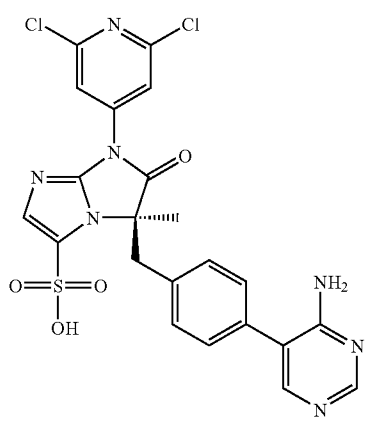 | (R)-5-[4-(4-Amino-pyrimidin-5-yl)-benzyl]-7-(2,6-dichloro-pyridin-4-yl)-5-methyl-6-oxo-6,7-dihydro-5H-imidazo[1,2-a]imidazole-3-sulfonic acid |

TABLE I-continued

| Compound Number | STRUCTURE | NAME |
|---|---|---|
| 22 | 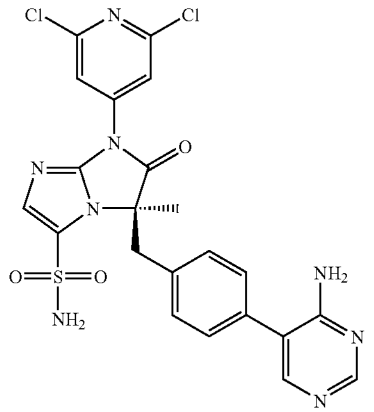 | (R)-5-[4-(4-Amino-pyrimidin-5-yl)-benzyl]-7-(2,6-dichloro-pyridin-4-yl)-5-methyl-6-oxo-6,7-dihydro-5H-imidazo[1,2-a]imidazole-3-sulfonic acid amide |
| 23 | 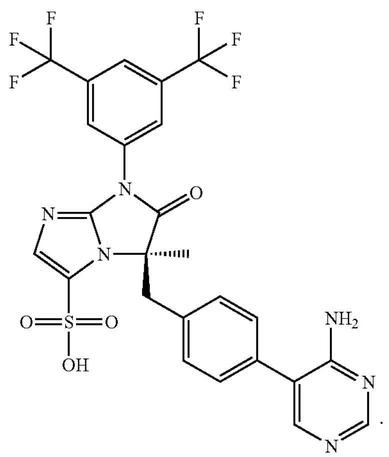 | (R)-5-[4-(4-Amino-pyrimidin-5-yl)-benzyl]-7-(3,5-bis-trifluoromethyl-phenyl)-5-methyl-6-oxo-6,7-dihydro-5H-imidazo[1,2-a]imidazole-3-sulfonic acid |
| 24 | 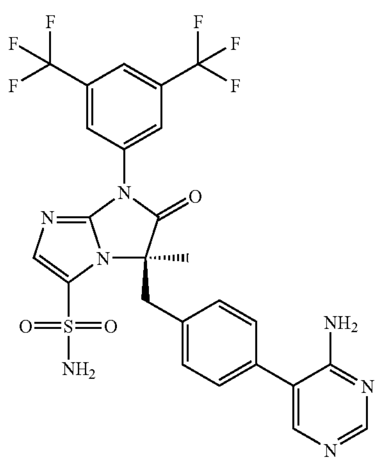 | (R)-5-[4-(4-Amino-pyrimidin-5-yl)-benzyl]-7-(3,5-bis-trifluoromethyl-phenyl)-5-methyl-6-oxo-6,7-dihydro-5H-imidazo[1,2-a]imidazole-3-sulfonic acid amide |

The present invention also includes all the pharmaceutically acceptable salts of the compounds of the formula I. The pharmaceutically acceptable salts includes any pharmaceutically-acceptable acid addition salts and pharmaceutically-acceptable base addition salts as would be understood by one skilled in the art. The compounds of the present invention therefore include the free base or acid thereof, their pharmaceutically acceptable salts and also may include oxidized sulfur atoms or quaternized nitrogen atoms in their structure, although not explicitly stated or shown, particularly the pharmaceutically acceptable forms thereof Such forms, particularly the pharmaceutically acceptable forms, are intended to be embraced by the present invention.

Some of the compounds of the present invention can exist in more than one tautomeric form, and the present invention therefore includes all such tautomers. In general, all tautomeric forms and isomeric forms and mixtures, whether individual geometric isomers or stereoisomers or racemic or non-racemic mixtures of isomers, of a chemical structure or compound is intended, unless the specific stereochemistry or isomeric form is specifically indicated in the compound name or structure.

Also included within the scope of the invention are the compounds of formula (I), including the subgeneric and specific embodiments thereof, in a substantially pure form. By the term "substantially pure" in the context of the present invention is meant a compound of formula (I) in an isolated form containing less than about 5%, more preferably less than about 1%, of other compounds or impurities. Such isolated forms can be readily obtained using conventional isolation and purification techniques well known in the art once the crude product of formula (I) is obtained according to the synthetics methods described herein. Such conventional isolation and purification techniques include, for example, recrystallization, filtration, washing, chromatography on silica gel, HPLC, etc.

General Synthetic Methods

Compounds of the invention may be prepared by the general methods described below. Optimum reaction conditions and reaction times for each individual step may vary depending on the particular reactants employed. Unless otherwise specified, solvents, temperatures and other reaction conditions may be readily selected by one of ordinary skill in the art. Specific procedures are provided in the Synthetic Examples section. Typically, reaction progress may be monitored by thin layer chromatography (TLC) if desired. If desired, intermediates and products may be purified by chromatography on silica gel and/or recrystallization, and characterized by one or more of the following techniques: NMR, mass spectroscopy and melting point. Starting materials and reagents are either commercially available or may be prepared by one skilled in the art from commercially available materials using methods described in the chemical literature.

Compounds of formula I may be prepared from intermediate II by the procedures set forth hereinafter.

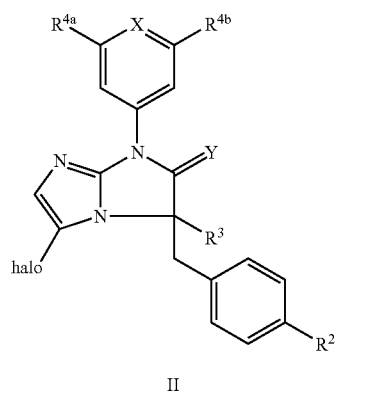

II

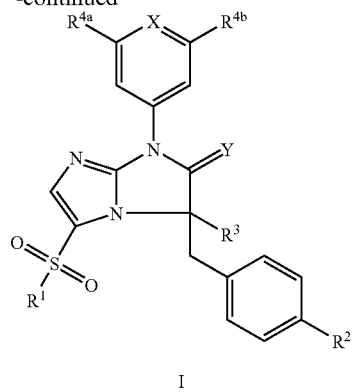

I

Method for Preparing Intermediate II

Intermediate II may be prepared by the procedure illustrated in Scheme I below, which procedure is also found in U.S. Pat. No. 6,844,360.

Scheme I

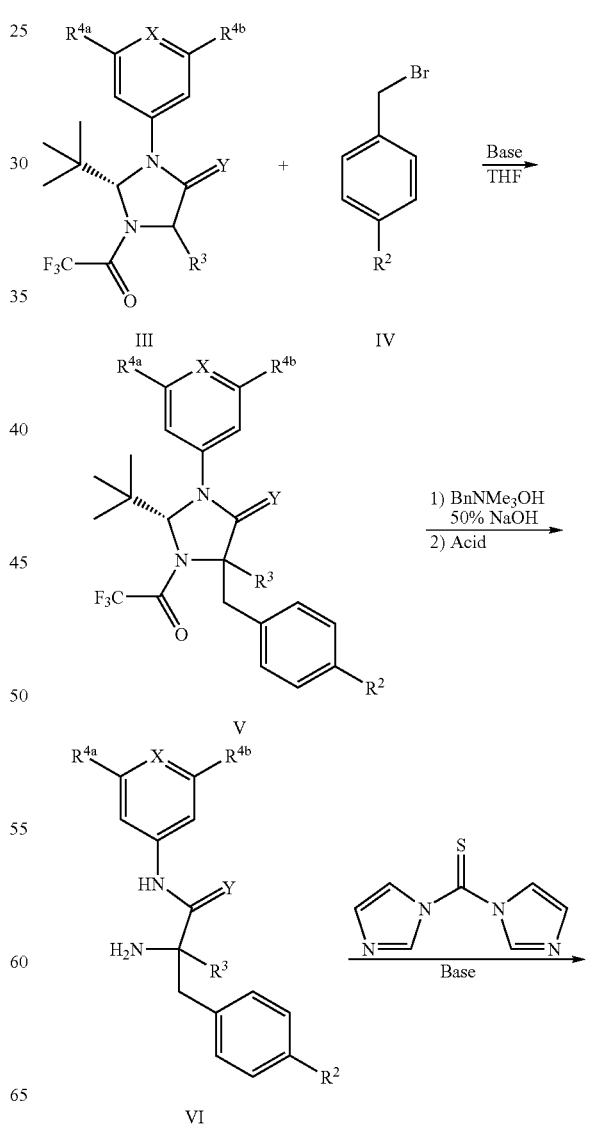

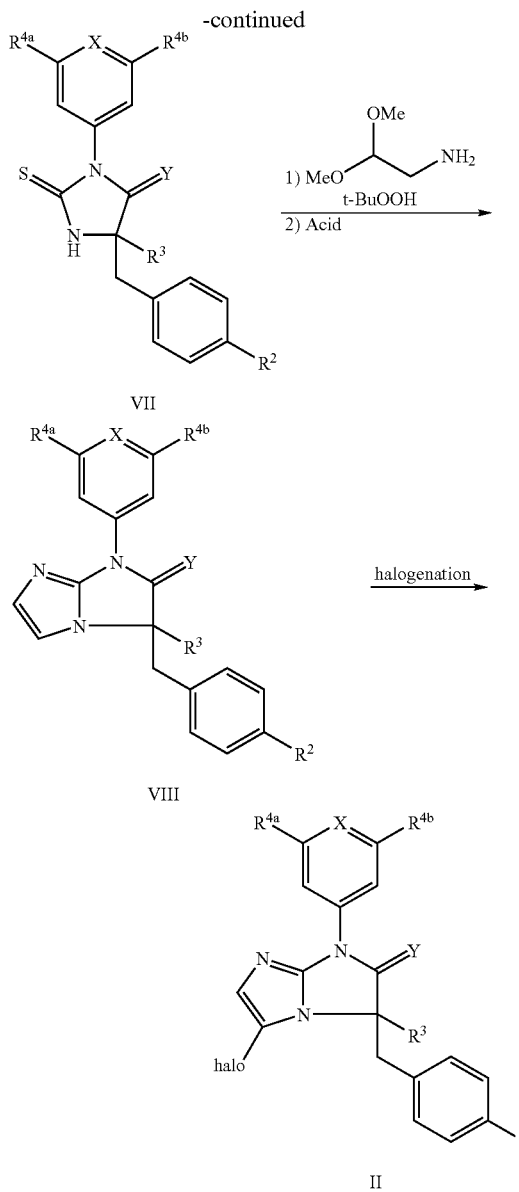

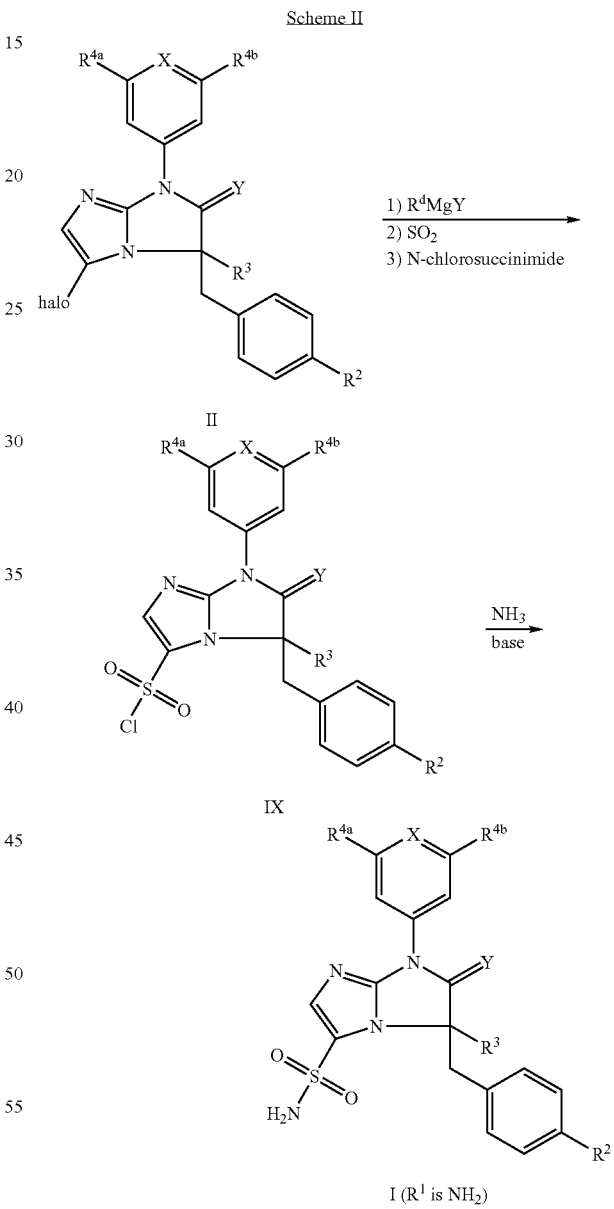

As illustrated above, intermediate III is deprotonated with a suitable base such as lithium bis(trimethylsilyl)amide at about −20° C. to −30° C., and then alkylated with a substituted benzyl halide, preferably a benzyl bromide (IV) to produce V. Hydrolysis of the trifluoroacetamide group of V, for example by treatment with 40% aqueous benzyltrimethylammonium hydroxide in dioxane/50% NaOH, followed by treatment with acid, such as HCl, provides VI. Treatment of VI with thiocarbonyldiimidazole in the presence of a base such as 4-(N,N-dimethylamino)pyridine provides VII. Treatment of VII with aminoacetaldehyde dimethyacetal and t-butylhydroperoxide solution, followed by treatment of the intermediate acetal with an acid such as p-toluenesulfonic acid provides VIII. Halogenation of VIII by treatment with an halogenating agent such as N-iodosuccinimide provides II.

The method used for preparation of intermediate III, treatment of the amide formed from N-Boc-D-alanine and 3,5-dichloroaniline with trifluoroacetic acid to remove the Boc-group, followed by treatment with pivalaldehyde, and acylation of the resulting imidazolodone with trifluoroacetic anhydride is described in U.S. Pat. No. 6,414,161, cited above, and in the chemical literature (N. Yee, Org. Lett., 2000, 2, 2781-2783).

Additional Methods for Preparing Intermediate II

The synthesis of intermediates II is also reported by Wu et al., U.S. Pat. No. 6,492,408, Frutos et al., U.S. Pat. No. 6,414,161, and Wang et al., U.S. Patent Application Publication No. 2006/0025447 A1.

Synthesis of Formula I Compounds where $R^1$ is $NH_2$

The synthesis of compounds of formula I wherein $R^1$ is $NH_2$ from intermediate II is illustrated in Scheme II.

As illustrated above, treatment of II with a Grignard reagent compound of the formula $R^dMgY$, where $R^d$ is $C_{1-6}$ alkyl or $C_{3-6}$cycloalkyl, and Y is halide, followed by treatment of the resulting magnesium salt with $SO_2$ and then N-chlorosuccinimide provides the sulfonyl chloride IX. Treatment of IX in a suitable solvent with ammonia (e.g., by the addition of ammonium hydroxide) in the presence of a suitable base provides the desired product of formula I. Alternatively, this two-step process can be performed efficiently in one-pot without isolation of the intermediate product IX. This one-pot variation comprises reacting a compound of the formula II with a compound of the formula $R^d MgY$ (where $R^d$ and Y are as defined above), sulfur dioxide and N-chlorosuccinimide, followed by a suitable base and ammonia (e.g., by the addition of ammonium hydroxide) in suitable solvent, to form a compound of the formula I without isolation of intermediates.

Suitable $R^d MgY$ include, for example, isopropylmagnesium chloride, isopropylmagnesium bromide, cyclopentylmagnesium chloride and cyclopentylmagnesium bromide.

When the $R^2$ group is 5-pyrimidyl it is necessary to pre-mix an organic base such as N,N,N',N'-tetramethylethylene diamine with $R^d MgY$, prior to reacting with the compound of formula II. This will prevent addition of $R^d MgY$ to the 5-pyrimidyl group.

Suitable solvents for this reaction include aprotic organic solvents, such as tetrahydrofuran.

Suitable bases for use in the second step of this reaction include, for example, triethylamine, diisopropylethylamine, potassium carbonate, cesium carbonate and sodium carbonate.

The addition of $R^d MgY$ is performed at a temperature of about −40° C. to about −15° C., preferably about −25° C. to about −15° C. The addition of sulfur dioxide and N-chlorosuccinimide is conducted at a temperature of about −40° C. to about −5° C., preferably about −15° C. to about −5° C.

Synthesis of Formula I Compounds where $R^1$ is OH

The synthesis of compounds of formula I wherein $R^1$ is OH from intermediate IX (prepared as in Scheme II) is illustrated in Scheme III.

The compound of formula IX is reacted with water, in a suitable solvent such as DMSO or dioxane, and then heated to obtain a sulfonic acid compound of formula I.

An alternative method for preparing compounds of formula I wherein $R^1$ is OH is illustrated in Scheme III' below:

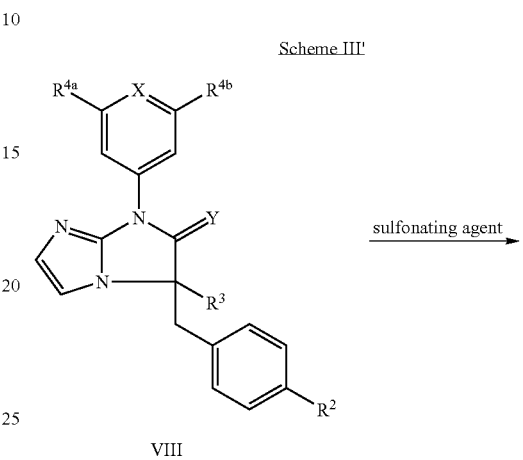

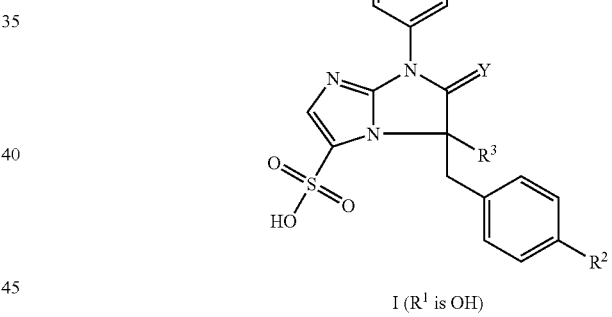

The compound of formula VIII (Scheme I) is reacted with a suitable sulfonating agent, such as an $SO_3$ pyridine complex, in a suitable solvent such as THF and then heated to obtain a sulfonated compound of formula I.

$R^2$ Group Variations

The desired $R^2$ on formula I compounds may be obtained by selection of the appropriately substituted intermediate IV in Scheme I. Alternately, one may prepare an intermediate VIII but having $R^2$ being Br (VIIIa) according to the procedure of Scheme I, which may then be converted to intermediates having $R^2$ being CN or a substituted 5-pyrimidyl group, for example, by the procedures illustrated in Scheme IV.

Scheme IV

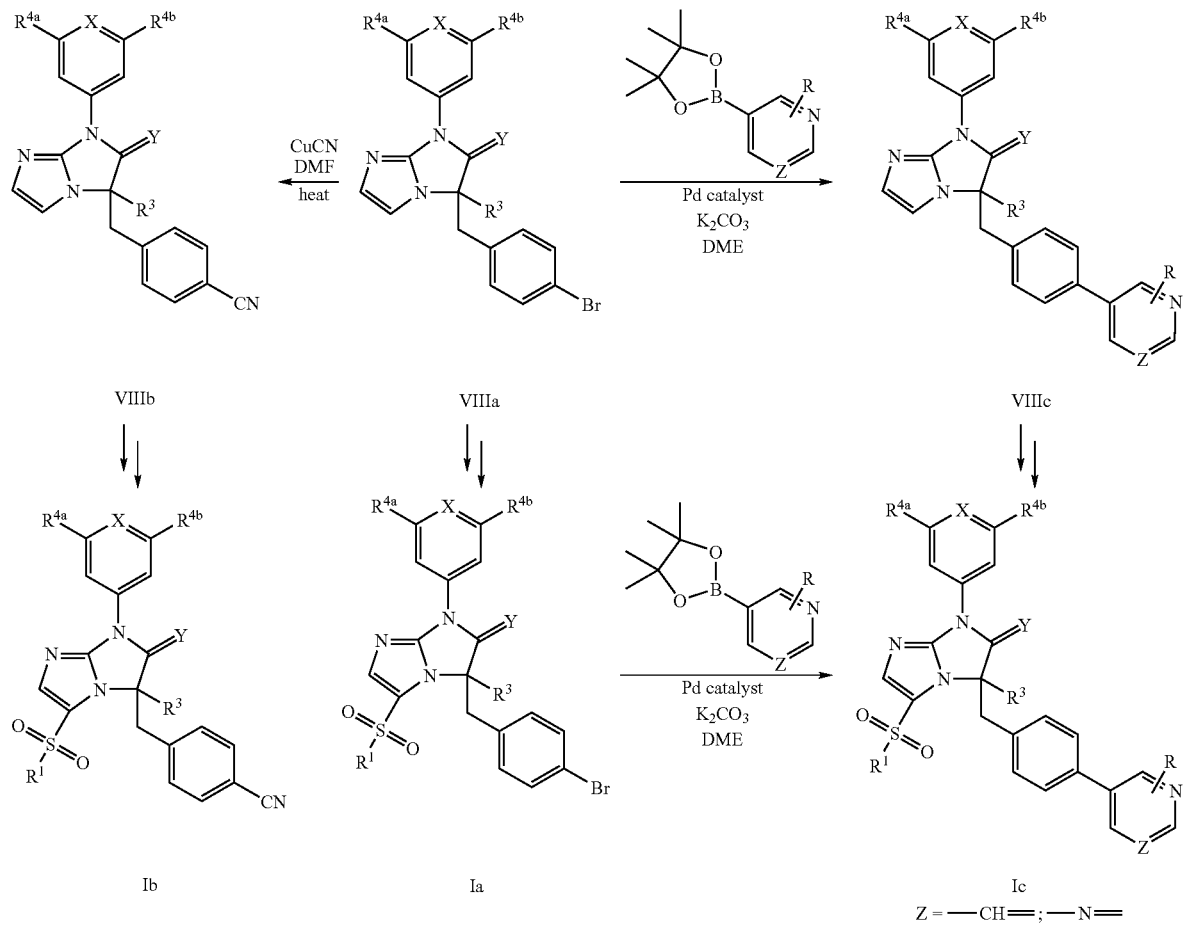

As illustrated above, the aryl bromide VIIIa is treated with a cyanide salt, preferably CuCN and heated in a suitable solvent such as DMF to provide the cyano-intermediate VIIIb. Treatment of VIIIa with a pyrimidine boronate ester such as 5-(4,4,5,5,-tetramethyl-[1,3,2]dioxaborolan-2-yl)-pyrimidine in the presence of a palladium catalyst such as [1,1'-bis(diphenylphosphino)ferrocene]dichloropalladium (II)·CH$_2$Cl$_2$ (PdCl$_2$(dppf)·CH$_2$Cl$_2$) and a base such as potassium carbonate in a suitable solvent (Suzuki reaction), for example dimethoxyethane, provides the pyrimidine intermediate VIIIc. Intermediates VIIIb and VIIIc may then be converted to desired compounds of formula I by the procedures described above. The Suzuki reaction to convert R$^2$=Br to R$^2$= an optionally substituted pyrimidine may also be carried out on a compound of formula I wherein R$^2$=Br (compound Ia). The Suzuki reaction may also be carried out in the reverse manner. The bromide VIIIa (or a compound of formula I with R$^2$=Br) may be converted to a boronate ester for example by treatment with bis(pinacolato)diboron in the presence of a palladium catalyst such as PdCl$_2$(dppf) and then reacted with the desired pyrimidyl bromide. The initial product of formula I may be further modified by methods known in the art to provide additional compounds of the invention.

Other features and advantages of the present invention will become apparent from the following more detailed examples which illustrate, by way of example, the principles of the invention.

SYNTHETIC EXAMPLES

Example 1

Synthesis of (R)-5-[4-(4-Amino-pyrimidin-5-yl)-benzyl]-7-(3,5-dichloro-phenyl)-5-methyl-6-oxo-6,7-dihydro-5H-imidazo[1,2-a]imidazole-3-sulfonic acid (1)

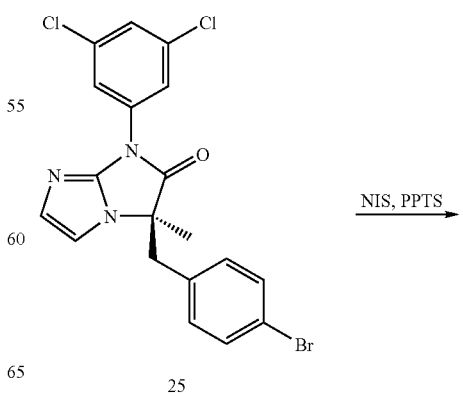

25

NIS, PPTS →

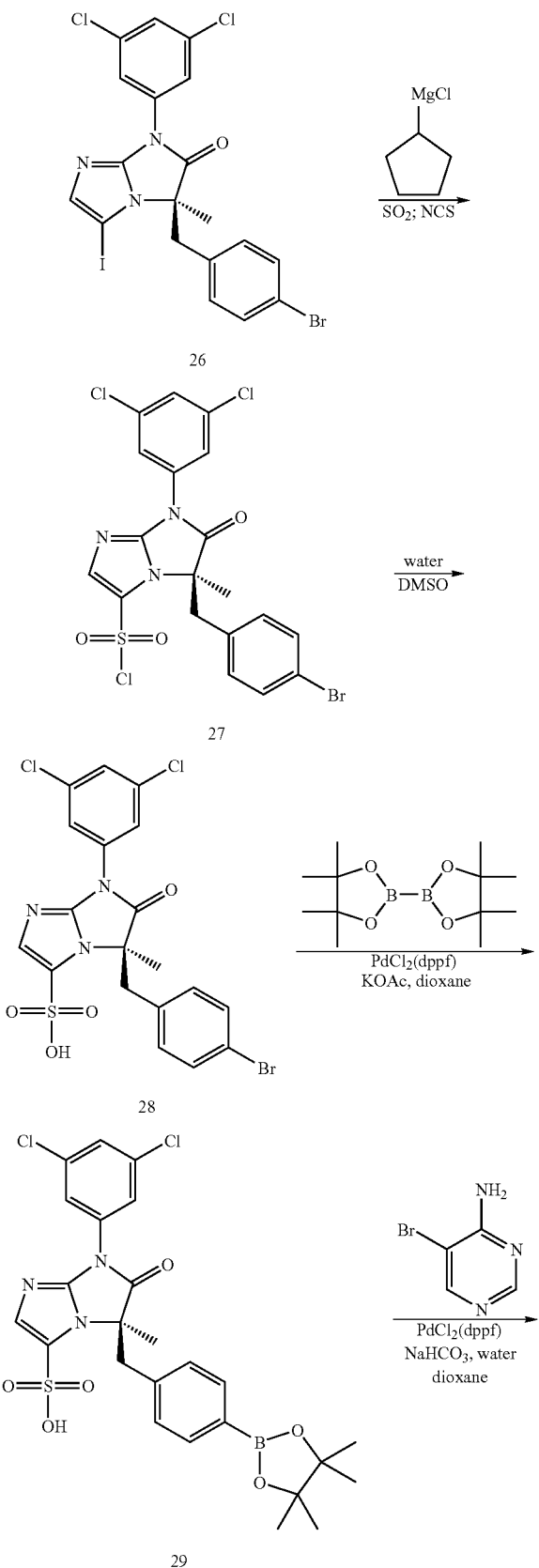
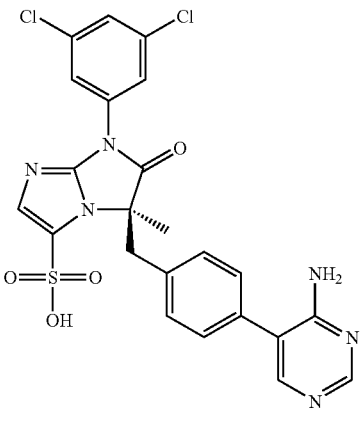

The synthesis of compound (25) is reported by Wu et al., U.S. Pat. No. 6,492,408 and Wang et al., U.S. Patent Application Publication No. 2006/0025447 A1, both incorporated herein by reference.

A solution of (R)-3-(4-bromo-benzyl)-1-(3,5-dichlorophenyl)-3-methyl-1H-imidazo[1,2-a]imidazol-2-one (25) in THF (0.12 M) is treated with N-iodosuccinimide (1.05 equiv) and pyridinium p-toluenesulfonate (0.1 equiv). The mixture is stirred at room temperature for 17 h, then diluted with EtOAc and washed with 10% $Na_2S_2O_3$ solution and water. The combined aqueous layers are extracted with EtOAc. The combined organic phases are washed with brine, dried over $Na_2SO_4$, filtered and concentrated. The crude oil is purified by silica gel chromatography to provide the desired iodide (26).

A solution of the above iodide (26) in THF (0.12 M) is cooled at −40° C. as c-pentyl magnesium chloride (1.05 equiv) is added dropwise over 10 min. After stirring at −40° C. for 1 h, $SO_2$ (g) is added by placing an inlet needle just above the surface of the reaction mixture for 1.5 min. The reaction mixture is warmed to −20° C. over 1 h and then stirred at room temperature for 1 h. $N_2$ (g) is bubbled through the mixture for 20 min followed by concentration and pumping under high vacuum for 12 h. The resulting foam is dissolved in THF (0.1 M) and cooled at −20° C. as a solution of N-chlorosuccinimide (1.2 equiv) in THF (0.3 M) is added dropwise over 5 min. After stirring at −20° C. for 1 h, the mixture is poured over ice and extracted with two portions of EtOAc. The combined organic layers are washed with ice-cold brine, dried over $Na_2SO_4$, filtered and concentrated. Purification by silica gel chromatography provides sulfonyl chloride (27) as a solid.

Sulfonyl chloride (27) (727 mg) is added to a DMSO (4.4 mL) and water (0.7 mL) mixture and then heated at 80° C. for 3 hr. The resultant homogeneous reaction is cooled to room temperature and diluted with 15 mL of water forming a precipitate. The solid is collected via vacuum filtration and air dried overnight yielding a quantitative yield of sulfonic acid (28).

Sulfonic acid (28) (826 mg) is dissolved in anhydrous dioxane (15.6 mL) and $N_2$ is bubbled through the solution for 20 min. Bis(pinacolato)diboron (474 mg), PdCl$_2$(dppf)·CH$_2$Cl$_2$ (127 mg) and KOAc (610 mg) are added together as a solid mixture. The reaction is flushed with N$_2$ and heated at 80° C. for 16 hr under an N$_2$ atmosphere. After cooling to room temperature the reaction is diluted with water and extracted with 10% EtOAc/hexanes to remove less polar materials. The aqueous phase is then extracted with EtOAc. The combined EtOAc layers are dried with MgSO$_4$ and concentrated to give 953 mg of the pinacol boronate (29) as a dark foam and is used without further purification.

A suspension of pinacol boronate (29) (506 mg), 4-amino-5-bromopyrimidine (189 mg) and Na$_2$CO$_3$ (123 mg) in a dioxane (5.2 mL) water (2.6 mL) mixture is degasses with N$_2$ for 20 minutes. PdCl$_2$(dppf)·CH$_2$Cl$_2$ (59 mg) is added and the reaction mixture is flushed with N$_2$ The reaction is heated to 80° C. for 15 hr, then cooled to rt, diluted with water (10 mL) and brine (10 mL) and extracted with EtOAc. The combined organic layers are dried with $_{MgSO4}$, filtered and concentrated. The material obtained is purified via reverse phase HPLC. The solvent is removed via lyophilization to give 120 mg of the title compound (1) as a white solid. (MS 544.95 M+1)

Example 2

Synthesis of (R)-5-[4-(4-Amino-pyrimidin-5-yl)-benzyl]-7-(3,5-dichloro-phenyl)-5-methyl-6-oxo-6,7-dihydro-5H-imidazo[1,2-a]imidazole-3-sulfonic acid amide (2)

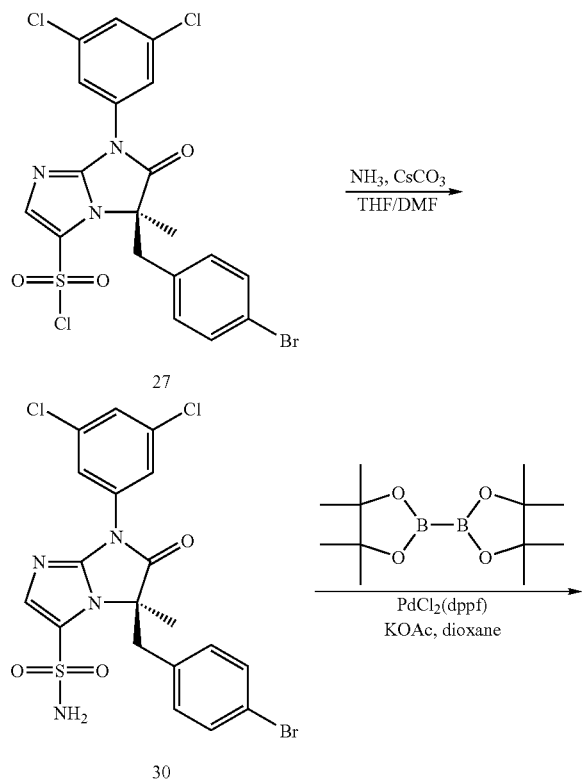

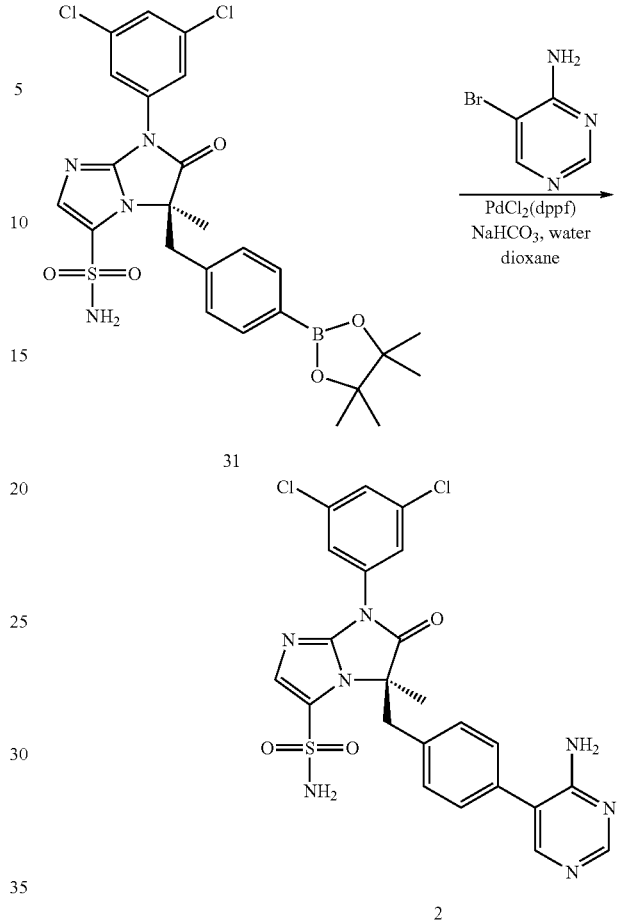

Sulfonyl chloride (27) (750 mg) is dissolved in a THF (2.5 mL) and DMF (0.5 mL) mixture at room temperature. CsCO$_3$ (667 mg) is added in one portion followed by concentrated NH$_4$OH (0.6 mL). The resulting solution is stirred at room temperature for 1 hr. The reaction is diluted with water and extracted with EtOAc. The combined organic layers are concentrated and purified via chromatography to give 495 mg of sulfonamide (30).

Sulfonamide (30) (495 mg) is dissolved in anhydrous dioxane (9.3 mL) in a screw cap vial. The solution is frozen and then put under vacuum for 25 min while it partially thawed. The solution is placed under N$_2$ and the bis(pinacolato)diboron (284 mg), Pd catalyst (38 mg) and KOAc (275 mg) are added together as a solid mixture. The reaction is flushed with N$_2$ and sealed with a cap and parafilm and heated at 80° C. for 20 hr. The solvent is lyophilized and the residue is purified via flash chromatography to give 407 mg of the pinacol boronate (31) as a foam.

Pinacol boronate (31) (204 mg), 4-amino-5-bromopyrimidine (92 mg) and Na$_2$CO$_3$ (52 mg) are suspended in a dioxane (2.2 mL) and water (1.1 mL) in a vial. N$_2$ is bubbled through the mixture for 20 minutes. The Pd catalyst (2.9 mg) is added and the vial is flushed with N$_2$, capped and sealed with parafilm. The reaction is heated to 80° C. for 18 hr. The reaction is cooled to rt, diluted with water (8 mL) and extracted with EtOAc. The combined organic layers are dried with MgSO4 and concentrated. The residue is purified via chromatography to afford 49.0 mg of the title compound. This material is further purified by reverse phase HPLC. The solvent is removed by lyophilization to give 44.3 mg of the trifluoroacetic acid salt of the desired amino pyrimidine (2) as a white powder. (MS 544.23 M+1)

Compounds (3)-(16) set forth in Table I above may be prepared in a manner analogous to that described above for compounds (1) and (2).

Compounds (21)-(24) set forth in Table I above may be prepared in a manner analogous to that described above for compounds (1) and (2) using the necessary reagents.

Example 3

Synthesis of (R)-7-(3,5-Dichloro-phenyl)-5-methyl-6-oxo-5-(4-trifluoromethoxy-benzyl)-6,7-dihydro-5H-imidazo[1,2-a]imidazole-3-sulfonic acid (17)

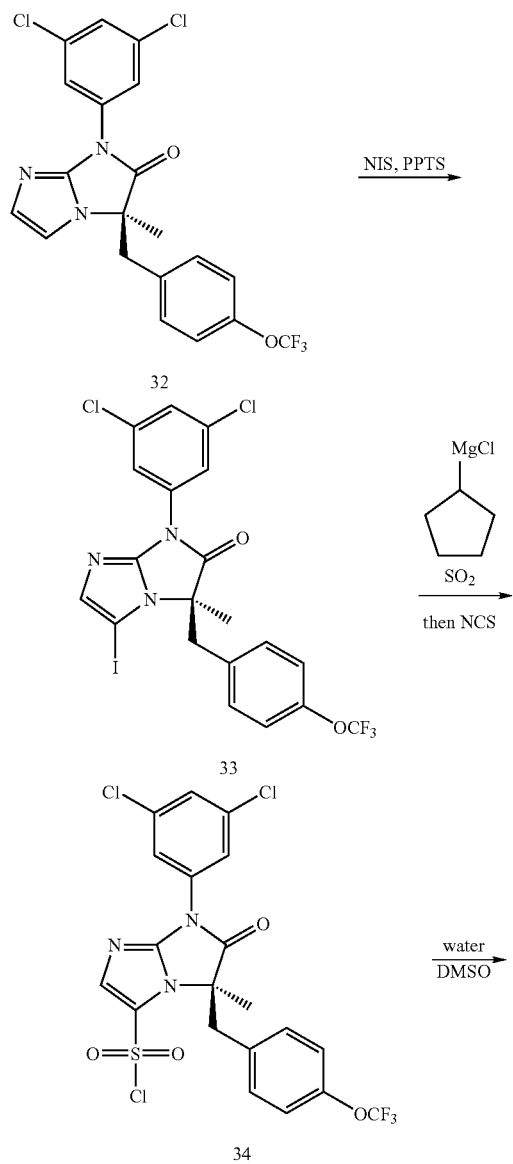

-continued

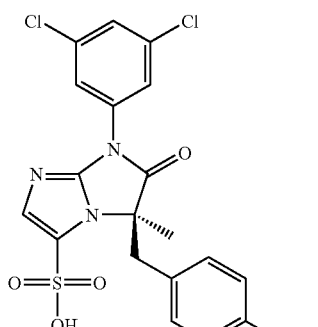

Compound (32) is prepared in a manner analogous to that described for compound (25).

A solution of (R)-1-(3,5-dichloro-phenyl)-3-methyl-3-(4-trifluoromethoxy-benzyl)-1H-imidazo[1,2-a]imidazol-2-one (32) (1.54 g) in THF (30 mL) is treated with N-iodosuccinimide (0.846 g) and pyridinium p-toluenesulfonate (0.086 g). The mixture is stirred at room temperature for 17 h, then diluted with EtOAc and washed with 10% $Na_2S_2O_3$ solution and water. The combined aqueous layers are extracted with EtOAc. The combined organic phases are washed with brine, dried over $Na_2SO_4$, filtered and concentrated. The crude oil is purified via silica gel chromatography to provide 1.27 g of compound (33) as an oil. (MS 582.0, M+1)

A solution of iodide (33) (1.24 g) in THF (16 mL) is cooled at −40° C. as cyclopentyl magnesium chloride (1.17 mL, 2 M in diethyl ether) is added dropwise over 10 min. After stirring at −40° C. for 1 h, $SO_2$ (g) is added by placing an inlet needle just above the surface of the reaction mixture for 1.5 min. The reaction mixture is warmed to −20° C. over 1 h and then stirred at room temperature for 1 h. $N_2$ (g) is bubbled through the mixture for 20 min followed by concentration and pumping under high vacuum for 12 h. The resulting foam is dissolved in THF (16 mL) and cooled at −20° C. as a solution of N-chlorosuccinimide (0.341 g) in THF (8 mL) is added dropwise over 5 min. After stirring at −20° C. for 1 h, the mixture is poured over ice and extracted with EtOAc. The combined organic layers are washed with ice-cold brine, dried over $Na_2SO_4$, filtered and concentrated. Purification via silica gel chromatography provided 0.975 g of compound (34) as a thick oil. (MS 554.2, M+1)

Sulfonyl chloride (34) (500 mg) is added to a DMSO (4.4 mL) and water (0.7 mL) mixture and then heated at 80° C. for 3 hr. The resultant homogeneous reaction is cooled to room temperature and diluted with 15 mL of water forming a precipitate. The solid is collected via vacuum filtration and air dried overnight providing 462 mg of sulfonic acid (17). (MS 535.9 M+1)

Example 4

Synthesis of (R)-7-(3,5-Dichloro-phenyl)-5-methyl-6-oxo-5-(4-trifluoromethoxy-benzyl)-6,7-dihydro-5H-imidazo[1,2-a]imidazole-3-sulfonic acid amide (18)

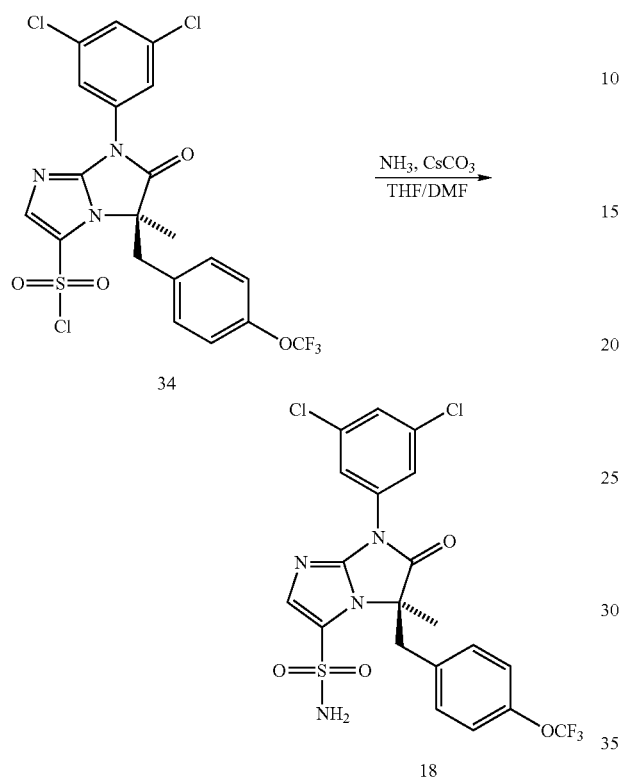

To a solution of sulfonyl chloride (34) (1.0 g) in a mixture of THF and DMF (4.0 ml, 5:1 by volume) is added $Cs_2CO_3$ (0.89 g) followed by ammonium hydroxide (0.9 ml, 28% solution in water) at room temperature. After 30 min, the mixture is treated with water and extracted with EtOAc. The extract is concentrated, and the residue is purified by chromatography on silica gel to afford 647 mg of sulfonamide (18). (MS 534 M+1)

Example 5

(R)-5-(4-Cyano-benzyl)-7-(3,5-dichloro-phenyl)-5-methyl-6-oxo-6,7-dihydro-5H-imidazo[1,2-a]imidazole-3-sulfonic acid (19)

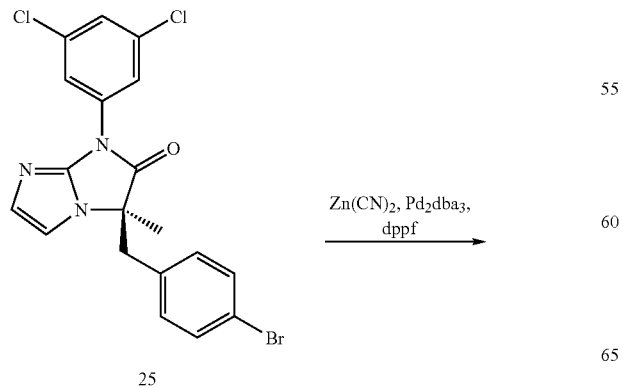

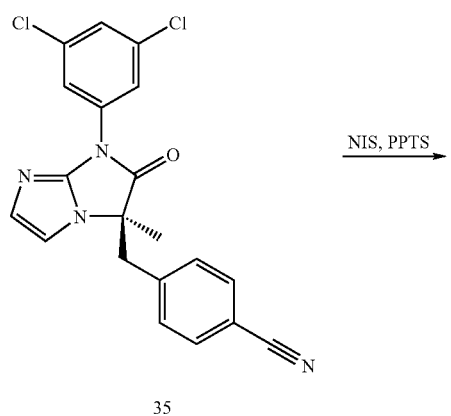

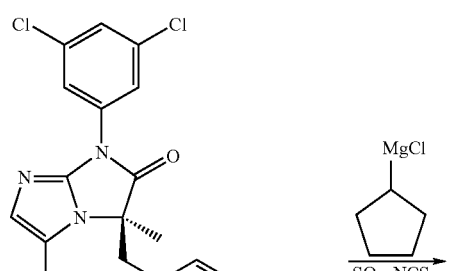

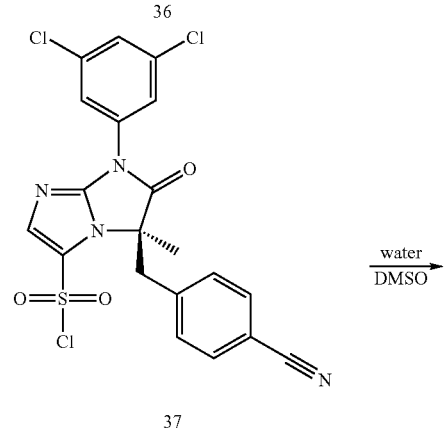

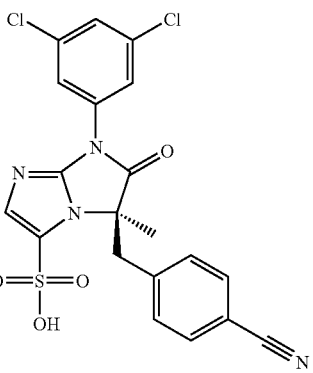

To a solution of (R)-3-(4-bromo-benzyl)-1-(3,5-dichloro-phenyl)-3-methyl-1H-imidazo[1,2-a]imidazol-2-one (25) (10.0 g) in DMF (200 mL) is added Zn(CN)$_2$ (1.58 g). The resulting solution is degassed with a stream of N$_2$ for 2 h. Pd$_2$dba$_3$ (1.02 g) and dppf (1.48 g) are added and the reaction mixture is heated to 120° C. for 2 h. The solvent is evaporated and the residue dissolve in EtOAc, then is washed with water and brine, then is dried and filtered and the residue is purified over Florisil to afford 7.0 g of compound (35).

To a cold (−30° C.) stirred solution of compound (35) (4.0 g) in CH$_2$Cl$_2$ (80 mL) is added pyridinium p-toluenesulfonate (0.25 g) and N-iodosuccinimide (2.9 g) portion wise over 30 min. The temperature of the bath is slowly raised to room temperature and stirred overnight. The reaction mixture is washed with 10% NaHSO$_3$ and water. The organic phase is dried over Na$_2$SO$_4$ and concentrated. The resulting crude product is purified via chromatography to afford 3.5 g of the iodide (36).

To a cold (−40° C.) solution of iodide (36) (1.0 g) in THF (10 mL) is added c-pentyl-magnesium chloride (1.5 mL, 2 M in Et$_2$O) drop wise over 10 min. The mixture is stirred at −40° C. for 1 hr, then SO$_2$ (g) is added by placing an inlet needle just above the surface of the reaction mixture for 1 min. The resulting solution is warmed to −20° C. over 1 h and then stirred at room temperature for an additional 1 h. N$_2$ (g) is bubbled through the mixture for 20 min followed by concentration and pumping under high vacuum for 12 h. The resulting foam is dissolved in THF (10 mL) and cooled at −20° C. as a solution of N-chlorosuccinimide (0.3 g) in THF (10 mL) is added over 1 min. The mixture is stirred at −20° C. for 1 h, then is poured over ice/water and extracted with EtOAc. The combined organic layers are washed with brine, dried over Na$_2$SO$_4$, filtered and concentrated. The crude product is purified via chromatography to give 0.65 g of the sulfonyl chloride (37).

Sulfonyl chloride (37) (70 mg) is added to a DMSO (1 mL) and water (0.2 mL) mixture and then heated at 80° C. for 3 hr. The resultant homogeneous reaction is cooled to room temperature and diluted with water and the aqueous layer extracted with EtOAc The combined organic layers are washed with brine, dried over Na$_2$SO$_4$, filtered and concentrated. The residue is purified via chromatography to provide 58 mg of sulfonic acid (19). (MS 477 M+1)

Example 6

(R)-5-(4-Cyano-benzyl)-7-(3,5-dichloro-phenyl)-5-methyl-6-oxo-6,7-dihydro-5H-imidazo[1,2-a]imidazole-3-sulfonic acid amide (20)

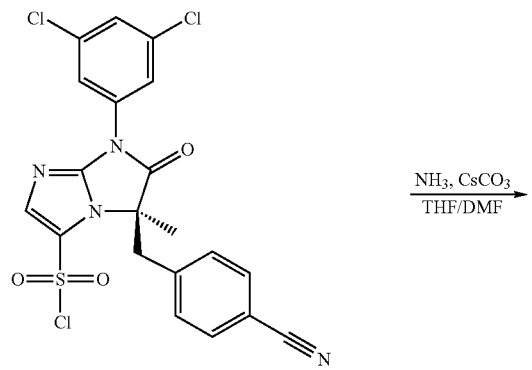

37

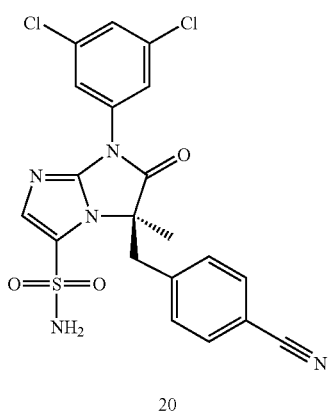

20

To a solution of sulfonyl chloride (37) (495 mg) in a mixture of THF (1 mL) and DMF (0.2 mL) is added CsCO$_3$ (0.24 g) followed by NH$_4$OH (0.24 mL). The reaction mixture is stirred at room temperature for 30 min and then treated with water. The aqueous layer is extracted with Et$_2$O and the organic phase is washed with water and brine, dried over Na$_2$SO$_4$, filtered, and concentrated. The crude product is purified via chromatography to give 100 mg of the title compound. (MS 475.9 M+1)

Description of Biological Properties

The biological properties of the compounds of the formula I may be investigated by way of the experimental protocol described below.

Assay to Determine Inhibition of LFA-1 Binding to ICAM-1

Purpose of Assay:

This assay protocol is designed to study the direct antagonism, by a test compound, of the interaction of the CAM, ICAM-1 with the Leukointegrin CD18/CD11a (LFA-1).

Description of Assay Protocol:

LFA-1 is immunopurified using the TS2/4 antibody from a 20 g pellet of human JY or SKW3 cells, utilizing a protocol previously described (Dustin, M. J.; et al., *J. Immunol.* 1992, 148, 2654-2660). The LFA-1 is purified from SKW3 lysates by immunoaffinity chromatography on TS2/4 LFA-1 mAb Sepharose and eluted at pH 11.5 in the presence of 2 mM MgCl$_2$ and 1% octylglucoside. After collection and neutralization of fractions from the TS2/4 column, samples are pooled and precleared with Protein G agarose.

A soluble form of ICAM-1 is constructed, expressed, purified and characterized as previously described (Marlin, S.; et al., *Nature,* 1990, 344, 70-72 and see Arruda, A.; et al., *Antimicrob. Agents Chemother.* 1992, 36, 1186-1192). Briefly, isoleucine 454 which is located at the putative boundary between domain 5 of the ectodomain and the transmembrane domain, is changed to a stop codon using standard oligonucleotide-directed mutagenesis. This construction yields a molecule identical with the first 453 amino acids of membrane bound ICAM-1. An expression vector is created with a hamster dihydrofolate reductase gene, a neomycin-resistance marker, and the coding region of the sICAM-1 construct described above, along with the promoter, splice signals, and polyadenylation signal of the SV40 early region. The recombinant plasmid is transfected into CHO DUX cells using standard calcium phosphate methods. Cells are passaged in selective media (G418) and colonies secreting sICAM-1 are amplified using methotrexate. sICAM-1 is purified from serum-free media using traditional non-affinity chromatographic techniques, including ion exchange and size exclusion chromatography.

LFA-1 binding to ICAM-1 is monitored by first incubating sICAM-1 at 40 µg/mL in Dulbecco's phosphate buffered saline with calcium and magnesium, additional 2 mM $MgCl_2$ and 0.1 mM PMSF (Diluting Buffer) in a 96-well plate for 30 min at room temperature. Plates are then blocked by the addition of 2% (w/v) bovine serum albumin in Diluting Buffer for 37° C. for 1 h. Blocking solution is removed from wells, and test compounds are diluted and then added followed by the addition of approximately 25 ng of immunoaffinity purified LFA-1. The LFA-1 is incubated in the presence of test compound and ICAM-1 at 37° C. for 1 h. Wells are washed 3 times with Diluting Buffer. The bound LFA-1 is detected by the addition of a polyclonal antibody directed against a peptide corresponding to the CD18 cytoplasmic tail in a 1:100 dilution with Diluting Buffer and 1% BSA and allowed to incubate for 45 min at 37° C. Wells are washed 3 times with Diluting Buffer and the bound polyclonal antibody is detected by the addition of a 1:4000 dilution of horse radish peroxidase conjugated to goat immunoglobulin directed against rabbit immunoglobulin. This reagent is allowed to incubate for 20 min at 37° C., wells are washed as above and the substrate for the horse radish peroxidase is added to each well to develop a quantitative colorimetric signal proportional to the amount of LFA-1 bound to sICAM-1. Soluble ICAM-1 (60 µg/mL) is used as a positive control for inhibition of the LFA-1/ICAM-1 interaction. The lack of the addition of LFA-1 to the binding assay is used as a background control for all samples. A dose-response curve is obtained for all test compounds.

Representative compounds of formula I selected from those set forth in Table I above were tested in this assay and each found to have a $K_d$<10 µM.

Description of Therapeutic Use

The novel small molecules of formula I provided by the invention inhibit the ICAM-1/LFA-1 dependent homotypic aggregation of human lymphocytes and human lymphocyte adherence to ICAM-1. These compounds have therapeutic utility in the modulation of immune cell activation/proliferation, e.g. as competitive inhibitors of intercellular ligand/receptor binding reactions involving CAMs and Leukointegrins. To be more specific, the compounds of the invention may be used to treat certain inflammatory conditions, including conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The compounds of the invention may also be used in treating asthma or as an adjunct to minimize toxicity with cytokine therapy in the treatment of cancers. In general these compounds may be employed in the treatment of those diseases currently treatable through steroid therapy.

Thus, another aspect of the invention is the provision of a method for the treatment or prophylaxis of the above-described conditions through the adminstration of therapeutic or prophylactic amounts of one or more compounds of the formula I.

In accordance with the method provided by the invention, the novel compounds of formula I may be administered for either a prophylactic or therapeutic purpose either alone or with other immunosuppressive or antiinflammatory agents. When provided prophylactically, the immunosuppressive compound(s) are provided in advance of any inflammatory response or symptom (for example, prior to, at, or shortly after the time of an organ or tissue transplant but in advance of any symptoms of organ rejection). The prophylactic administration of a compound of the formula I serves to prevent or attenuate any subsequent inflammatory response (such as, for example, rejection of a transplanted organ or tissue, etc.). The therapeutic administration of a compound of the formula I serves to attenuate any actual inflammation (such as, for example, the rejection of a transplanted organ or tissue). Thus, in accordance with the invention, a compound of the formula I can be administered either prior to the onset of inflammation (so as to suppress an anticipated inflammation) or after the initiation of inflammation.

The novel compounds of the formula I may, in accordance with the invention, be administered in single or divided doses by the oral, parenteral or topical routes. A suitable oral dosage for a compound of formula I would be in the range of about 0.1 mg to 10 g per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgment, who will use as criteria for fixing a proper dosage the size and condition of the patient as well as the patient's response to the drug.

The compounds of formula I are typically administered in the form of a pharmaceutical composition thereof further containing at least one pharmaceutically acceptable carrier or adjuvant. When the compounds of the present invention are to be administered by the oral route, they may be administered as medicaments in the form of pharmaceutical composition which contain them in association at least one compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical composition can be prepared in a conventional manner and finished dosage forms can be solid dosage forms, for example, tablets, dragees, capsules, and the like, or liquid dosage forms, for example solutions, suspensions, emulsions and the like. The pharmaceutical composition may be subjected to conventional pharmaceutical operations such as sterilization. Further, the pharmaceutical composition may contain one or more conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered topically or by suppository.

Formulations

Compounds of the formula I can be formulated for therapeutic administration in a number of ways. Descriptions of several exemplary formulations are given below.

Example A

| Capsules or Tablets | |
|---|---|
| Ingredients | Quantity |
| Example A-1 | |
| Compound of formula I | 250 mg |
| Starch | 160 mg |
| Microcrys. Cellulose | 90 mg |
| Sodium Starch Glycolate | 10 mg |
| Magnesium Stearate | 2 mg |
| Fumed colloidal silica | 1 mg |
| Example A-2 | |
| Compound of formula I | 50 mg |
| Dicalcium Phosphate | 160 mg |
| Microcrys. Cellulose | 90 mg |
| Stearic acid | 5 mg |
| Sodium Starch Glycolate | 10 mg |
| Fumed colloidal silica | 1 mg |

The compound of formula I is blended into a powder mixture with the premixed excipient materials as identified above with the exception of the lubricant. The lubricant is then blended in and the resulting blend compressed into tablets or filled into hard gelatin capsules.

Example B

| Parenteral Solutions | |
|---|---|
| Ingredients | Quantity |
| Compound of formula I | 500 mg |
| PEG 400 | 40% by volume |
| Ethyl Alcohol | 5% by volume |
| Saline | 55% by volume |

The excipient materials are mixed and then added to one of the compounds of formula I in such volume as is necessary for dissolution. Mixing is continued until the solution is clear. The solution then filtered into the appropriate vials or ampoules and sterilized by autoclaving.

Example C

| Suspension | |
|---|---|
| Ingredients | Quantity |
| Compound of formula I | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water and thereafter one of the compounds of formula I is added and mixing is continued until the suspension is homogeneous. The suspension is then transferred into the appropriate vials or ampoules.

Example D

| Topical Formulation | |
|---|---|
| Ingredients | Quantity |
| Compound of formula I | 5% by weight |
| Tefose 63 | 13% by weigth |
| Labrafil M 1944 CS | 3% by weight |
| Paraffin Oil | 8% by weight |
| Methylparaben (MP) | 0.15% by weight |
| Propylparaben (PP) | 0.05% by weight |
| Deionized water | q.s. to 100 |

The proper amounts of Tefose 63, Labrafil M 1944 CS, Paraffin oil and water are mixed and heated at 75° C. until all components have melted. The mixture is then cooled to 50° C. with continuous stirring. Methylparaben and propylparaben are added with mixing and the mixture is cooled to ambient temperature. The compound of formula I is added to the mixture and blended well.

What is claimed is:

1. A compound of the following formula (I):

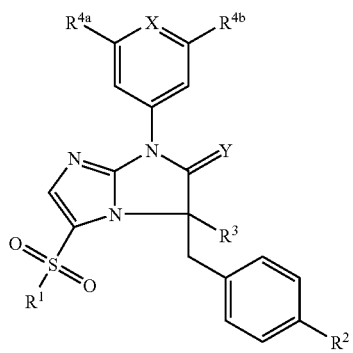

wherein:
$R^1$ is: OH;
$R^2$ is:
  (A) aryl selected from the group consisting of pyridyl and pyrimidyl, wherein one or more hydrogen atoms of said aryl group are independently substituted with moieties selected from the group consisting of:
    (i) cyano,
    (ii) halogen and
    (iii) groups of the formula $-NR^{13}R^{14}$, wherein $R^{13}$ and $R^{14}$ are each, independently, hydrogen or straight or branched alkyl of 1 to 3 carbon atoms;
  (B) trifluoromethoxy or,
  (C) cyano;
$R^3$ is straight or branched alkyl of 1 to 3 carbon atoms;
$R^{4a}$ is halogen or alkyl of 1 to 2 carbon atoms substituted by one or more halogen atoms;
$R^{4b}$ is halogen or alkyl of 1 to 2 carbon atoms substituted by one or more halogen atoms;
X is $-CH=$ or $-N=$; and
Y is an oxygen or sulfur atom;
or a pharmaceutically acceptable salt thereof.

2. A compound of the formula I, in accordance with claim 1, wherein $R^2$ is:
  (A) aryl selected from the group consisting of 3-pyridyl and 5-pyrimidyl, wherein said aryl group is mono-, di- or tri-substituted with:
    (i) cyano;
    (ii) halogen; or
    (iii) $NH_2$;
  (B) trifluoromethoxy; or
  (C) cyano, or a pharmaceutically acceptable salt thereof.

3. A compound of the formula I, in accordance with claim 1, wherein $R^2$ is:
  (A) aryl selected from the group consisting of 3-pyridyl and 5-pyrimidyl wherein said aryl group is monosubstituted with:
    (i) cyano or
    (ii) $NH_2$,
  (B) trifluoromethoxy; or
  (C) cyano; or a pharmaceutically acceptable salt thereof.

4. A compound of the formula I, in accordance with claim 1, wherein $R^2$ is:
  (A) 5-pyrimidyl monosubstituted with $NH_2$;
  (B) trifluoromethoxy or
  (C) cyano; or a pharmaceutically acceptable salt thereof.

5. A compound of the formula I, in accordance with claim 1, wherein $R^3$ is methyl or ethyl; or a pharmaceutically acceptable salt thereof.

6. A compound of the formula I, in accordance with claim 1, wherein $R^3$ is methyl; or a pharmaceutically acceptable salt thereof.

7. A compound of the formula I, in accordance with claim 1, wherein $R^{4a}$ and $R^{4b}$ are each selected from Cl or $CF_3$; or a pharmaceutically acceptable salt thereof.

8. A compound of the formula I, in accordance with claim 1, wherein $R^{4a}$ and $R^{4b}$ are each Cl, or a pharmaceutically acceptable salt thereof.

9. A compound of the formula I, in accordance with claim 1, wherein $R^{4a}$ and $R^{4b}$ are each $CF_3$; or a pharmaceutically acceptable salt thereof.

10. A compound of the formula I, in accordance with claim 1, wherein X is $-CH-$; or a pharmaceutically acceptable salt thereof.

11. A compound of the formula I, in accordance with claim 1, wherein X is $-N=$; or a pharmaceutically acceptable salt thereof.

12. A compound of the formula I, in accordance with claim 1, having the absolute stereochemistry depicted below by formula I*:

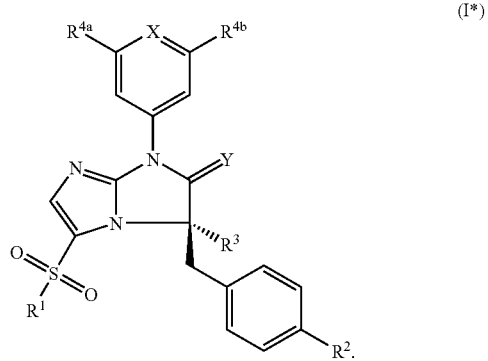

13. A compound of formula (I) according to claim 1, selected from a subgeneric embodiment I-22 to I-33 as set forth in the following table, wherein the variable group identifiers (Ai) to (Gii) in the table are defined according to the definitions (Ai) to (Gii) set forth below the table:

| Embodiment | $R^1$ | $R^2$ | $R^3$ | $R^{4a}$ | $R^{4b}$ | X | Y |
|---|---|---|---|---|---|---|---|
| I-22 | Ai | Bi | Ci | Di | Ei | Fi | Gi |
| I-23 | Ai | Bii | Ci | Di | Ei | Fi | Gi |
| I-24 | Ai | Biii | Ci | Di | Ei | Fi | Gi |
| I-25 | Ai | Biii | Cii | Di | Ei | Fi | Gi |
| I-26 | Ai | Biii | Cii | Dii | Eii | Fi | Gi |
| I-27 | Ai | Biii | Cii | Dii | Eii | Fi | Gii |
| I-28 | Ai | Biii | Cii | Dii | Eii | Fii | Gi |
| I-29 | Ai | Biii | Cii | Dii | Eii | Fii | Gii |
| I-30 | Ai | Biii | Cii | Dii | Eiii | Fi | Gi |
| I-31 | Ai | Biii | Cii | Dii | Eiii | Fi | Gii |
| I-32 | Ai | Biii | Cii | Dii | Eiii | Fii | Gi |
| I-33 | Ai | Biii | Cii | Dii | Eiii | Fii | Gii |

(A) Definitions of $R^1$:
(Ai) $R^1$ is OH;
(B) Definitions of $R^2$:
(Bi) $R^2$ is:
  (A) aryl selected from the group consisting of 3-pyridyl and 5-pyrimidyl,
    wherein said aryl group is mono-, di- or tri-substituted with:
    (iv) cyano;
    (v) halogen; or
    (vi) $NH_2$;
  (B) trifluoromethoxy; or
  (C) cyano;
(Bii) $R^2$ is:
  (A) aryl selected from the group consisting of 3-pyridyl and 5-pyrimidyl wherein said aryl group is monosubstituted with:

(i) cyano or
(ii) NH₂,
(B) trifluoromethoxy; or
(C) cyano;
(Biii) R² is: (A) 5-pyrimidyl monosubstituted with NH₂:
(B) trifluoromethoxy or
(C) cyano;
(C) Definitions of R³:
(Ci) R³ is methyl or ethyl;
(Cii) R³ is methyl;
(D) Definitions of R$^{4a}$:
(Di) R$^{4a}$ is Cl or CF₃;
(Dii) R$^{4a}$ is Cl;
(E) Definitions of R$^{4b}$:
(Ei) R$^{4b}$ s Cl or CF₃;
(Eii) R$^{4b}$ is Cl;
(Eiii) R$^{4b}$ is CF₃;
(F) Definitions of X:
(Fi) X is —CH—;
(Fii) X is —N=; and
(G) Definitions of Y:
(Gi) Y is oxygen;
(Gii) Y is sulfur.

14. A compound of formula (I) according to claim 1, selected from the compounds set forth in the following table or the pharmaceutically acceptable salts thereof:

| Compound Number | STRUCTURE |
|---|---|
| 1 | 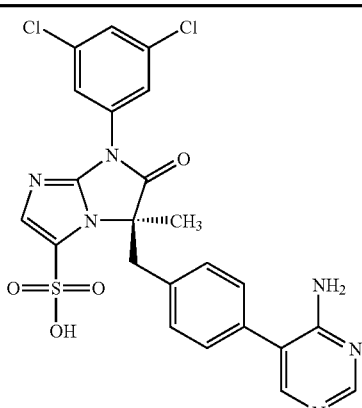 |
| 3 | 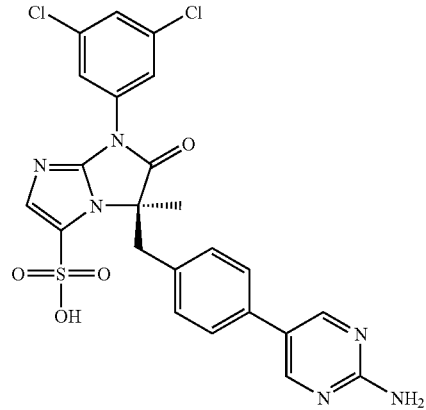 |
| 5 | 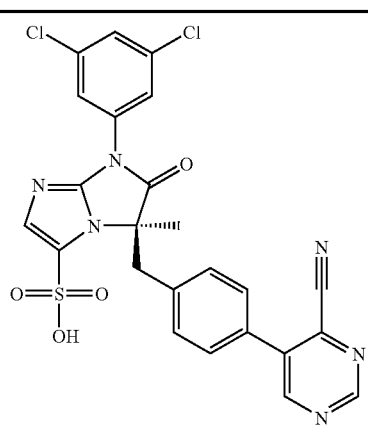 |
| 7 | 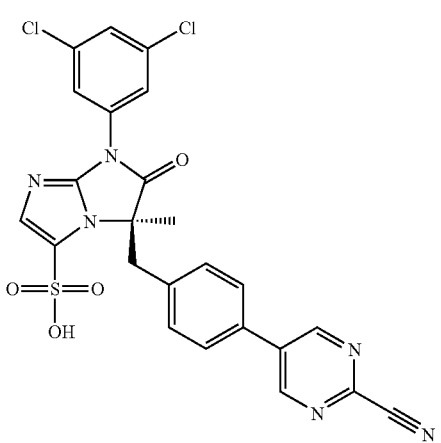 |
| 9 | 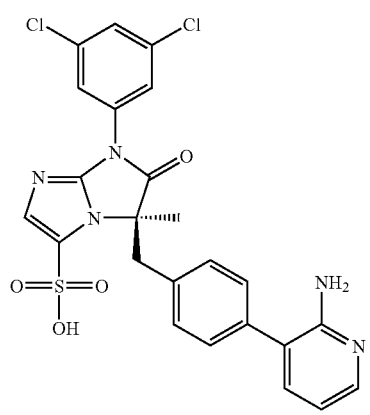 |

-continued
| Compound Number | STRUCTURE |
|---|---|
| 11 | 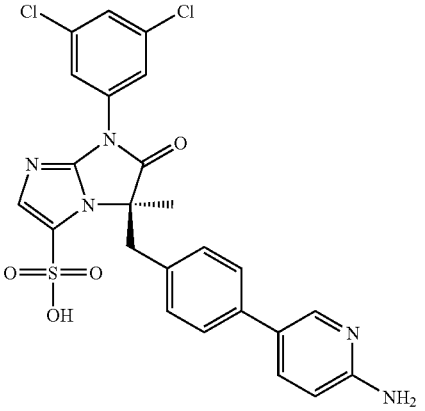 |
| 13 | 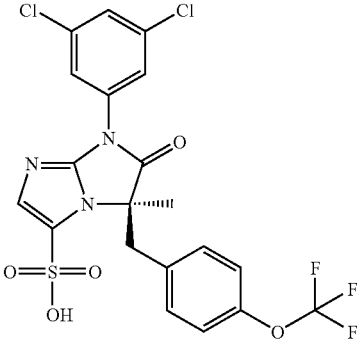 |
| 15 | 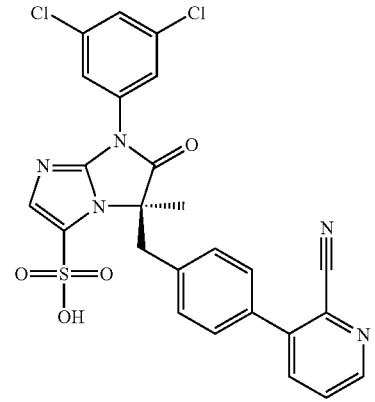 |
-continued
| Compound Number | STRUCTURE |
|---|---|
| 17 | 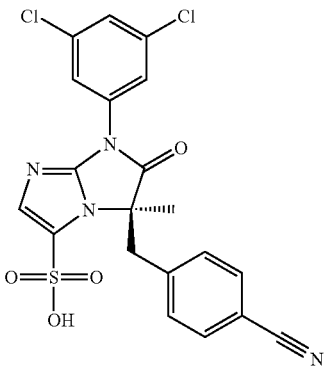 |
| 19 | 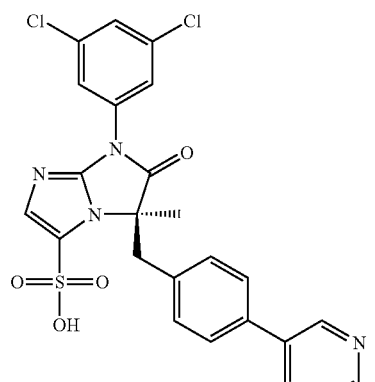 |
| 21 | 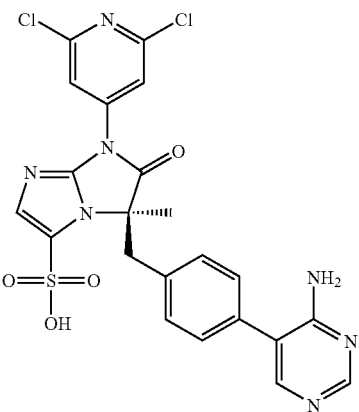 |
| 23 | 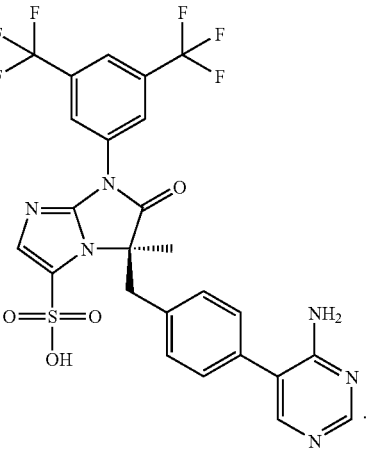 |

15. A compound of formula (I), in accordance with claim 1, in substantially pure form.

16. A compound of formula (I), in accordance with claim 14, in substantially pure form.

17. A pharmaceutical composition comprising a compound in accordance with claim 1 and at least one pharmaceutically acceptable carrier or adjuvant.

18. A method for treating an inflammatory condition by inhabiting the ICAM-1/LFA-1 dependent homotypic aggregation of human lymphocytes and human lymphocyte adherence to ICAM-1 in a patient which comprises administering to said patient a therapeutically effective amount of a compound in accordance with claim 1.

19. The method of claim 18 wherein the patient to be treated has psoriasis or multiple sclerosis.

* * * * *